(12) United States Patent
Mazmanian et al.

(10) Patent No.: US 10,772,918 B2
(45) Date of Patent: Sep. 15, 2020

(54) PROBIOTIC PREVENTION AND TREATMENT OF COLON CANCER

(71) Applicant: California Institute of Technology, Pasadena, CA (US)

(72) Inventors: Sarkis K. Mazmanian, Porter Ranch, CA (US); Yunkyung Lee, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/514,796

(22) Filed: Jul. 17, 2019

(65) Prior Publication Data

US 2019/0336545 A1  Nov. 7, 2019

Related U.S. Application Data

(63) Continuation of application No. 14/274,607, filed on May 9, 2014, now abandoned.

(60) Provisional application No. 61/822,126, filed on May 10, 2013.

(51) Int. Cl.
| | | |
|---|---|---|
| *A61K 35/741* | (2015.01) | |
| *A61K 31/715* | (2006.01) | |
| *A61K 31/59* | (2006.01) | |

(52) U.S. Cl.
CPC ............ *A61K 35/741* (2013.01); *A61K 31/59* (2013.01); *A61K 31/715* (2013.01)

(58) Field of Classification Search
None
See application file for complete search history.

(56) References Cited

U.S. PATENT DOCUMENTS

| | | | |
|---|---|---|---|
| 4,775,626 A | 10/1988 | Armenta et al. | |
| 5,571,900 A | 11/1996 | Wiegand et al. | |
| 5,679,654 A | 10/1997 | Tzianabos et al. | |
| 5,700,787 A | 12/1997 | Tzianabos et al. | |
| 6,358,939 B1 | 3/2002 | Hayes et al. | |
| 7,026,285 B2 | 4/2006 | Tzianabos et al. | |
| 7,083,777 B1 | 8/2006 | Tzianabos et al. | |
| 7,384,645 B2 | 6/2008 | Foster et al. | |
| 7,629,330 B2 | 12/2009 | Wang et al. | |
| 8,206,726 B2 | 6/2012 | Kasper et al. | |
| 2003/0044425 A1 | 3/2003 | Burt et al. | |
| 2003/0147865 A1 | 8/2003 | Salomon et al. | |
| 2003/0147922 A1 | 8/2003 | Capiau et al. | |
| 2005/0013831 A1 | 1/2005 | Foster et al. | |
| 2005/0020515 A1* | 1/2005 | Graff ................. | A61K 31/7036 514/35 |
| 2005/0048587 A1 | 3/2005 | Rao et al. | |
| 2005/0063979 A1 | 3/2005 | Pickl et al. | |
| 2006/0275752 A1 | 12/2006 | Sindhi | |
| 2008/0057565 A1 | 3/2008 | Comstock et al. | |
| 2009/0017472 A1 | 1/2009 | Stuhlmuller et al. | |
| 2009/0252708 A1 | 10/2009 | Fitzpatrick et al. | |
| 2009/0317410 A1 | 12/2009 | Wang et al. | |
| 2010/0275282 A1 | 10/2010 | Round et al. | |
| 2010/0311686 A1* | 12/2010 | Kasper ................. | A61K 31/715 514/54 |
| 2010/0330166 A1 | 12/2010 | Ishida et al. | |
| 2011/0251156 A1 | 10/2011 | Shen et al. | |
| 2011/0287048 A1 | 11/2011 | Round et al. | |
| 2012/0087895 A1 | 4/2012 | Mazmanian et al. | |
| 2013/0039949 A1 | 2/2013 | Mazmanian | |
| 2013/0064859 A1 | 3/2013 | Mazmanian | |
| 2013/0121966 A1 | 5/2013 | Mazmanian et al. | |
| 2013/0195802 A1* | 8/2013 | Moore ................... | A61K 35/74 424/93.2 |

FOREIGN PATENT DOCUMENTS

| | | |
|---|---|---|
| CN | 1818061 A | 8/2006 |
| DE | 3704389 A1 | 8/1988 |
| EP | 371414 A2 | 6/1990 |
| EP | 382576 A1 | 8/1991 |
| EP | 497524 A2 | 8/1992 |

(Continued)

OTHER PUBLICATIONS

Garrett et al. (Cell Host and Microbe vol. 8, pp. 292-300, Sep. 2010 (Year: 2010).*
Pragani et al. J. Am. Chem. Soc. vol. 133, pp. 102-107, 2011 (Year: 2011).*
"Asthma" from the Centers for Disease Control and Prevention, [retrieved Nov. 13, 2012]. Retrieved from the Internet www.cdc.gov/asth ma/aag/2010/overview.html.
"Ulcerative Colitis" from the National Institutes of Health [online], [retrieved Nov. 9, 2012]. Retrieved from the internet <http://digestive.niddk.nih.gov/ddiseases/pubs/colitis/UlcerativeColitis_508.pdf>.
[No Author Listed] "MS the Disease". National Multiple Sclerosis Society. Downloaded from the internet at http://www.nationalmssociety.org/About-the-Society/Press-Room/MS-the-Disease on Dec. 19, 2016, 4 pages (website copyright 2014).

(Continued)

*Primary Examiner* — Jana A Hines
*Assistant Examiner* — Khatol S Shahnan Shah
(74) *Attorney, Agent, or Firm* — Sheppard, Mullin, Richter & Hampton LLP

(57) ABSTRACT

Methods are provided herein for preventing, delaying the onset of or reducing the progression of colorectal tumorigenesis in a subject identified as at risk of colorectal tumorigenesis, comprising adjusting the composition of gut microbiota in the subject via administering to the subject a composition comprising *Bacteroides* bacteria or administering to the subject a therapeutically effective amount of a pharmaceutical composition comprising zwitterionic polysaccharide (ZPS). In another aspect, methods are provided for treating or ameliorating a colorectal cancer in a subject, comprising adjusting the composition of gut microbiota in the subject having the colorectal cancer. In a further aspect, methods are provided for relieving gastrointestinal (GI) distress of a subject having a colorectal condition, comprising: determining the colorectal condition of the subject; and relieving GI distress in the subject by adjusting the composition of gut microbiota in the subject.

20 Claims, 3 Drawing Sheets

Specification includes a Sequence Listing.

(56) References Cited

FOREIGN PATENT DOCUMENTS

| | | |
|---|---|---|
| EP | 1358885 A1 | 11/2003 |
| EP | 1459757 A1 | 9/2004 |
| GB | 2286193 A | 8/1995 |
| JP | S56128721 A | 10/1981 |
| JP | H10507746 A | 7/1998 |
| JP | 2002540074 A | 11/2002 |
| JP | 2002541113 A | 12/2002 |
| JP | 2003204796 A | 7/2003 |
| JP | 2004536028 A | 12/2004 |
| JP | 2010059201 A | 3/2010 |
| WO | WO 95/31990 A1 | 11/1995 |
| WO | WO 96/07427 A1 | 3/1996 |
| WO | WO 96/32119 A1 | 10/1996 |
| WO | WO 96/35433 A1 | 11/1996 |
| WO | WO 98/42718 A1 | 10/1998 |
| WO | WO 98/45335 A1 | 10/1998 |
| WO | WO 00/01733 A1 | 1/2000 |
| WO | WO 00/59515 A2 | 10/2000 |
| WO | WO 02/07741 A1 | 1/2002 |
| WO | WO 02/45708 A2 | 6/2002 |
| WO | WO 03/075953 A2 | 9/2003 |
| WO | WO 03/077863 A2 | 9/2003 |
| WO | WO 03/095606 A2 | 11/2003 |
| WO | WO 2004/050909 A2 | 6/2004 |
| WO | WO 2004/089407 A2 | 10/2004 |
| WO | WO 2005/010215 A2 | 2/2005 |
| WO | WO 2005/094571 A1 | 10/2005 |
| WO | WO 2007/040446 A1 | 4/2007 |
| WO | WO 2008/095141 A2 | 8/2008 |
| WO | WO 2009/062132 A2 | 5/2009 |
| WO | WO 2009/149149 A1 | 12/2009 |
| WO | WO 2010/124256 A2 | 10/2010 |
| WO | WO 2011/056703 A1 | 5/2011 |
| WO | WO 2011/127302 A2 | 10/2011 |
| WO | WO 2011/146910 A1 | 11/2011 |
| WO | WO 2011/153226 A | 12/2011 |
| WO | WO 2012/027032 A1 | 3/2012 |
| WO | WO 2012/103532 A1 | 8/2012 |
| WO | WO 2013/009945 A1 | 1/2013 |
| WO | WO 2013/019896 A1 | 2/2013 |
| WO | WO 2013/036290 | 3/2013 |
| WO | WO 2013/052099 A2 | 4/2013 |
| WO | WO 2014/182966 A1 | 11/2014 |

OTHER PUBLICATIONS

[No Author Listed] Drug Absorption, Bioavailability, and Routes of Administration. Goodman & Oilman's The Pharmacological Basis of Therapeutics, Tenth Edition, McGraw-Hill Medical Publishing Edition, New York, 2001, pp. 5-8.
[No Author Listed] Progress in Autoimmune Diseases Research. National Institutes of Health. The Autoimmune Diseases Coordinating Committee. Report to Congress. U.S. Department of Health and Human Service. Mar. 2005. 146 pages.
Abreu, M.T. et al. "Measurement of vitamin D levels in inflammatory bowel disease patients reveals a subset of Crohn's disease patients with elevated 1,25-dihydroxy vitamin D and low bone mineral density" Gut, 2004, 53(8) pp. 1129-1136.
Adams JS, et al. (2008) Unexpected actions of vitamin D: new perspectives on the regulation of innate and adaptive immunity. Nat Clin Pract Endocrinol Metab 4: 80-90.
Adams JS, et al. (2012) Extrarenal expression of the 25-hydroxyvitamin D-1-hydroxylase. Archives of biochemistry and biophysics 523: 95-102.
Adkins, B. et al "Exclusive Th2 Primary Effector Function in Spleens but Mixed Th1/Th2 Function in Lymph Nodes of Murine Neonates" Journal Immunology 2000; 164:2347-2353.
Advisory Action for U.S. Appl. No. 13/112,725, filed May 20, 2011 on behalf of June L. Round, dated Mar. 4, 2014. 3 pages.
Aharoni et al., Bystander suppression of experimental autoimmune encephalomyelitis by T cell lines and clones of the type induced by copolymer 1. J Neuroimmunol. Nov. 2, 1998;91(1-2):135-46.

Aharoni et al., Copolymer 1 induces T cells of the T helper type 2 that crossreact with myelin basic protein and suppress experimental autoimmune encephalomyelitis. Proc Natl Acad Sci USA. Sep. 30, 1997;94(20):10821-6.
Al-Bader et al. "Activation of Human Dendritic Cells Is Modulated by Components of the Outer Membranes of Neisseria meningitidis" Infection and Immunity. Oct. 2003; 71(10): 5590-5597).
Akbari et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.
Allen AC, et al. (2012) "A pilot study of the immunological effects of high-dose vitamin D in healthy volunteers". Multiple Sclerosis Journal; 2012; vol. 18; No. 12; pp. 1797-1800.
Anderson AC, et al. (2012) A transgenic model of central nervous system autoimmunity mediated by CD4+ and CD8+ T and B cells. Journal of immunology 188: 2084-2092.
Arnon et al., New insights into the mechanism of action of copolymer 1 in experimental allergic encephalomyelitis and multiple sclerosis. J Neural. Apr. 1996;243(4 Suppl I):S8-13. Review.
Asadullah et al., Interleukin-10 therapy-review of a new approach. Pharmacol Rev. Jun. 2003;55(2):241-69.
Ascherio A, et al. "Vitamin D and multiple sclerosis". Lancet Neurology; Jun. 2010; vol. 9: pp. 599-612.
Azzawi et al., Identification of activated T lymphocytes and eosinophils in bronchial biopsies instable a topic asthma. Am Rev Respir Dis. Dec. 1990; 142(6 Pt 1):1407-13.
Beacher-Allan CM, et al. (2011) CD2 costimulation reveals defective activity by human CD4+CD25(hi) regulatory cells in patients with multiple sclerosis. Journal of immunology 186: 3317-3326.
Banerjee et al. "Expansion of FOXP3 high regulatory T cells by human dendritic cells (DCs) in vitro and after injection of the cytokine-matured DCs in myeloma patients" Blood. 2006; 108: 2655-2661.
Baranzini SE, et al. (2010) Genome, epigenome and RNA sequences of monozygotic twins discordant for multiple sclerosis. Nature 464: 1351-1356.
Barnes, M.J., et al. (2009). "Regulatory T cells reinforce intestinal homeostasis". Immunity 31, 401-411.
Bar-On L, et al. (2010) Defining in vivo dendritic cell functions using CD11c-DTR transgenic mice. Methods in molecular biology 595: 429-442.
Barrat FJ, et al. (2002) In vitro generation of interleukin 10-producing regulatory CD4(+) T cells is induced by immunosuppressive drugs and inhibited by T helper type 1 (Th1)- and Th2-inducing cytokines. J Exp Med 195: 603-616.
Barutca et al., Prevention of interleukin-2-induced severe bronchospasm with salbutamol. J Aerosol Med. 2003 Summer;16(2):183-4.
Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.
Batta et al., Conformational stabilization of the altruronic acid residue in the O-specific polysaccharide of Shigella sonnei/Plesiomonas shigelloides. Carbohydr Res. Dec. 1998;305(1):93-9.
Bayley DP et al. Analysis of cepA and other Bacteroides fragilis genes reveals a unique promoter structure. (2000) FEMS Microbial Lett 193:149-54.
Bazan et al., Unraveling the structure of IL-2. Science. Jul. 17, 1992;257(5068):410-3.
Becker et al., "TGF—Suppresses Tumor Progression in Colon Cancer by Inhibition of IL-6 trans-Signaling," Immunity, vol. 21, 491-501 (2004).
Becker KG, et al. (1998) Clustering of non-major histocompatibility complex susceptibility candidate loci in human autoimmune diseases. Proc Natl Acad Sci U S A 95: 9979-9984.
Berer et al., Commensal gut flora and brain autoimmunity: a love or hate affair? Acta Neuropathol. May 2012;123(5):639-51. doi: 10.1007/s00401-012-0949-9. Epub Feb. 10, 2012.
Berer et al., Commensal microbiota and myelin autoantigen cooperate to trigger autoimmune demyelination. Nature. Oct. 26, 2011;479(7374):538-41. doi: 10.1038/nature10554.

(56) References Cited

OTHER PUBLICATIONS

Berggren et al., Decreasing serum concentrations of all-trans, 13-cis retinoic acids and retinal during fasting and caloric restriction. J Intern Med. Mar. 2003;253(3):375-80.
Bernatowska-Matuszkiewicz et al., IgG subclasses and antibody response to pneumococcal capsular polysaccharides in children with severe sinopulmonary infections and asthma. Immunol Investi. 1991;20(2):173-185.
Bettelli E, et al. (2003) Myelin oligodendrocyte glycoprotein-specific T cell receptor transgenic mice develop spontaneous autoimmune optic neuritis. The Journal of experimental medicine 197: 1073-1081.
Bettelli, E. et al. "Reciprocal developmental pathways for the generation of pathogenic effector TH17 and regulatory T cells" Nature vol. 441 pp. 235-238 (2006).
Bhaduri et al., Simple and rapid method for disruption of bacteria for protein studies. Appl Environ Microbial. Oct. 1983;46(4):941-3.
Bhat R, et al. (2009) Innate and adaptive autoimmunity directed to the central nervous system. Neuron 64: 123-132.
Blander et al., Toll-dependent selection of microbial antigens for presentation by dendritic cells. Nature. Apr. 6, 2006;440(7085):808-12. Epub Feb. 19, 2006.
Blomfield et al. Lrp stimulates phase variation of type 1 fimbriation in E. coli K12. J. Bacteriology 175, 27-36, 1993.
Blumberg & Powrie, "Microbiota, Disease, and Back to Health: A Metastable Journey," Sci. Transl. Med., vol. 4, 137rv7 (2012).
Boguniewicz, "The autoimmune nature of chronic urticarial", Allergy and Asthma Proceedings, vol. 29, No. 5, 2008; pp. 433-438.
Bollrath et al., "gp130-Mediated Stat3 Activation in Enterocytes Regulates Cell Survival and Cell-Cycle Progression during Colitis-Associated Tumorigenesis," Cancer Cell, vol. 15, 91-102 (2009).
Borsellino et al., Expression of ectonucleotidase CD39 by Foxp3+ Treg cells: hydrolysis of extracellular ATP and immune suppression. Blood. Aug. 15, 2007;110(4):1225-32. Epub Apr. 20, 2007.
Bouskra, D., et al. (2008). Lymphoid tissue genesis induced by commensals through NOD1 regulates intestinal homeostasis. Nature 456, 507-510.
Bregenholt, S. Cells and cytokines in the pathogenesis of inflammatory bowel disease: new insights from mouse T cell transfer models. Exp Clin Immunogenet 17, 115-29 (2000).
Brichford, Can You Prevent Multiple Sclerosis? Understanding factors that increase your risk of multiple sclerosis and what—if anything—you can do about them. EverydayHealth.com. Dec. 2008; 2 pages.
Brubaker et al., Mitogenic activity of purified capsular polysaccharide A from Bacteroides fragilis: differential stimulatory effect on mouse and rat lymphocytes in vitro. J Immunol. Feb. 15, 1999;162(4):2235-42.
Bruce D, et al. (2011) Converging pathways lead to overproduction of IL-17 in the absence of vitamin D signaling. International immunology 23: 519-528.
Brunkow, M.E., et al., "Disruption of a new forkhead/winged-helix protein, scurfin, results in the fatal lymphoproliferative disorder of the scurfy mouse" Nat Genet 27, 68-73 (2001).
Budinger et al., Immunologic mechanisms in hypersensitivity reactions to metal ions: an overview. Allergy. Feb. 2000;55(2):108-15. Review.
Burgers et al., The challenges of HIV vaccine development and testing. Best Pract Res Clin Obstet Gynaecol. Apr. 2005;19(2):277-91.
Byers et al., "Mechanism of action of vitamin D and the vitamin D receptor in colorectal cancer prevention and treatment," Rev. Endocr. Metab. Disord, Mar. 2012, pp. 31-38, vol. 13, Issue 1, Springer, Berlin, Germany.
Cabrera R, et al. (2010) Influence of serum and soluble CD25 (sCD25) on regulatory and effector T-cell function in hepatocellular carcinoma. Scandinavian journal of immunology 72: 293-301.
Campbell et al. The vitamin D receptor as a therapeutic target in Expert Opinion Ther. Targets, 2006; vol. 10; pp. 735-748.

Cantorna et al. "Vitamin D status, 1,25-dihydroxyvitamin D3, and the immune system" (Am. J. Clin. Nutr. 80(suppl):1717S-20S, 2004).
Cantorna MT, et al. (1996) "1,25-Dihydroxyvitamin D3 reversibly blocks the progression of relapsing encephalomyelitis, a model of multiple sclerosis". Proceedings of the National Academy of Sciences of the United States of America 93: 7861-7864.
Cash, H.L., et al. (2006). Symbiotic bacteria direct expression of an intestinal bactericidal lectin. Science 313, 1126-1130.
Catorna, M.T. et al. 1,25-Dihydroxycholecalciferol prevents and ameliorates symptoms of experimental murine inflammatory bowel disease. J. Nutr. 2000 130(11) oo.2648-52.
Chambers E. et al. (2011) The impact of vitamin D on regulatory T cells. Curr. Allergy Asthma Rep 11: 29-36.
Chang JH, et al. (2010) "1,25-Dihydroxyvitamin D3 inhibits the differentiation and migration of T(H)17 cells to protect against experimental autoimmune encephalomyelitis." PLoS One 5: e12925. 12 pages.
Chatila et al., Role of regulatory T cells in human diseases. J Allergy Clin Immunol. Nov. 2005;116(5):949-59; quiz 960.
Chen Jet al., DNA inversion on conjugative plasmid pVT745. J Bacterial. Nov. 2002; 184(21):5926-34.
Chen, X. et al. "Pertussis Toxin by Inducing IL-6 Promotes the Generation of IL-17-Producing CD4 Cells". Journal of Immunology, May 15, 2007, vol. 178, No. 10 pp. 6123-6129.
Chow J, et al. (2009) Getting the bugs out of the immune system: do bacterial microbiota "fix" intestinal T cell responses? Cell Host Microbe 5: 8-12.
Clemente et al., "Infliximab modifies mesenteric adipose tissue alterations and intestinal inflammation in rats with TNBS-induced colitis," Scand. J. Gastroenterol., vol. 47, 943-50 (2012).
Cobb et al., Zwitterionic capsular polysaccharides: the new MHCII-dependent antigens. Cell Microbial. Oct. 2005;7(10): 1398-403. Review.
Collison et al., The inhibitory cytokine IL-35 contributes to regulatory T-cell function. Nature. Nov. 22, 2007;450(7169):566-9.
Communication pursuant to Article 94(3) EPC for European Application No. 08847489.5, dated Aug. 7, 2013.
Comstock et al. Analysis of a capsular polysaccharide biosynthesis locus of Bacteroides fragilis. (1999) Infect Immun 67:3525-32.
Comstock et al., Bacterial glycans: key mediators of diverse host immune responses. Cell. Sep. 8, 2006;126(5):847-50.
Comstock et al., Interstrain variation of the polysaccharide B biosynthesis locus of Bacteroides fragilis: characterization of the region from strain 638R. J Bacterial. Oct. 1999 ;181(19):6192-6.
Conesa et al., Interleukin-2 induces peroxide production by primed normodense eosinophils of patients with asthma. Allergy Asthma Proc. Jan.-Feb. 2003;24(1):27-33.
Coombes JL, et al. (2007) Control of intestinal homeostasis by regulatory T cells and dendritic cells. Semin Immunol 19: 116-126.
Coombes, J.L., et al. (2007). A functionally specialized population of mucosal CD103+ DCs induces Foxp3+ regulatory T cells via a TGF-beta and retinoic acid-dependent mechanism. J Exp Med 204, 1757-1764.
Correale J, et al. (2011) Vitamin D-mediated immune regulation in multiple sclerosis. Journal of the neurological sciences 311: 23-31.
Couper et al. "IL-10: The Master Regulator of Immunity to Infection" Journal of Immunology. 2008; 180:5771-5777.
Coussens & Werb, "Inflammation and cancer," Nature, vol. 420, 860-867 (2002).
Coyne, M.J. et al, "Bacteroides fragilis NCTC9343 Produces at Least Three Distinct Capsular Polysaccharides: Cloning, Characterization, and Reassignment of Polysaccharide Band C Biosynthesis Loci", Infection and Immunity, Nov. 2000, p. 6176-6181.
Crabb et al., T cell regulation of Bacteroides fragilis-induced intraabdominal abscesses. Rev Infect Dis. Jan.-Feb. 1990;12 Suppl 2:S1 78-84. Review.
Craig, Autologous hematopoietic stem cell transplantation for Crohn's disease. Autoimmun Rev. Aug. 2002;1(4):244-9. Review.
Dadley-Moore, The sweet side of maturation. Nature Rev Immunol. Sep. 2005; 5:674.
Dahiyat BI. et al., De nova protein design: fully automated sequence selection. Science (1997) 278:82-87.

(56) References Cited

OTHER PUBLICATIONS

Daniel et al. Immune Modulatory Treatment of Trinitrobenzene Sulfonic Acid Colitis with Calcitriol is Associated with a Change of a T Helper (Th) 1/1Th17 to a Th2 and Regulatory T Cell Profile, in J. Pharmacology and Expet. Therapeutics, 2008, vol. 324, pp. 23-33.
Definition of "prevention" from the Institute for International Medical Education [online], [Retrieved on Mar. 24, 2011]. Retrieved from the internet. www.iime.org/glossary.htm. Published Feb. 2002, p. 1, 2, 26, 27 and 39.
Deib, Treating multiple sclerosis with monoclonal antibodies: a 2013 update. Expert Rev Neurother. Mar. 2013;13(3):313-35. doi: 10.1586/ern.13.17.
Denning, T. et al. "Lamina propria macrophages and dendritic cells differentially induce regulatory and interleukin 17-producing T cell responses" Nature Immunology; vol. 8; No. 10; Oct. 1, 2007; pp. 1086-1094.
Deslongchamps et al., "Ozonolysis of Acetals. (1) Ester Synthesis, (2) THP Ether Cleavage, (3) Selective Oxidation of B-Glycoside, (4) Oxidative Removal of Benzylidene and Ethylidene Protecting Groups". Canadian J of Chem. 1971; 49:2465-2467.
Deslongchamps et al., The Importance of Conformation in the Ozonolysis of Acetals. Canadian J Chem. 1972; 50:3402-3404.
Dias et al., Antisense oligonucleotides: Basic concepts and mechanisms. Mol. Cancer Therap., 2002, vol. 1: 347-355.
Difabio et al., Structure of the Capsular Polysaccharide Antigen of Type IV Group B *Streptococcus*; Can. J. Chem. 67:877 (1989).
Doig et al., The efficacy of the heat killing of Mycobacterium tuberculosis. J Clin Pathol. Oct. 2002;55(10):778-9.
Dooms et al., Revisiting the role of IL-2 in autoimmunity. Eur J Immunol. Jun. 2010;40(6):1538-40. doi: 10.1002/eji.201040617.
Duerr, R.H. et al. Science vol. 314; 2006; pp. 1461.
Eisenstein et al. Integration host factor is required for the DNA inversion that controls phase variation in *E. coli*. Proc Natl. Acad. Sci. 84, 6506-6510, 1987.
Elson, C. et al. "Monoclonal anti-interleukin 23 reverses active colitis in a T cell-mediated model in mice" Gastroenterology 132, 2359-70 (2007).
EP Communication 94.3 dated Aug. 7, 2013 for EP Application 08847489.5 filed on Nov. 9, 2008.
European Communication pursuant to Article 94(3) EPC dated Feb. 5, 2014 for European application 10767863.3 filed on Apr. 23, 2010.
European Communication pursuant to Rules 70(2) and 70a(2) EPC dated Dec. 27, 2010 for European application 08847489.5 filed on Nov. 9, 2008.
European Communication pursuant to Rules 70(2) and 70a(2) EPC dated Feb. 12, 2013 for European application 10767863.3 filed on Apr. 23, 2010.
European Search Report completed on Dec. 2, 2010 for European application 08847489 filed on Apr. 23, 2010.
Examination Report for European patent application No. 11784368.0, dated Jul. 8, 2016. 7 pages.
Extended European Search Report for Application No. 12811896.5, dated Jun. 1, 2015. 11 pages.
Extended European Search Report for European Application No. 08847489.5 dated Dec. 8, 2010. 8 pages.
Extended European Search Report for European Application No. 10767863.3 dated Jan. 24, 2013. 10 pages.
Extended European Search Report for European Application No. 12837738.9 dated Mar. 18, 2015 8 pages.
Falk, P.G., et al. (1998). Creating and maintaining the gastrointestinal ecosystem: what we know and need to know from gnotobiology. Microbiol Mol Biol Rev 62, 1157-1170.
Final Office Action for U.S. Appl. No. 12/267,602, filed Nov. 9, 2008 on behalf of Sarkis K. Mazmanian et al. dated Feb. 6, 2012. 15 pages.
Final Office Action for U.S. Appl. No. 12/766,787, filed Apr. 23, 2010 on behalf of June L. Round et al. dated Aug. 4, 2015. 29 pages.
Final Office Action for U.S. Appl. No. 12/766,787, filed Apr. 23, 2010 on behalf of June L. Round et al. dated Nov. 26, 2012. 12 pages.
Final Office Action for U.S. Appl. No. 12/831,131, filed Jul. 6, 2010 on behalf of June L. Round et al. dated Jun. 10, 2013. 23 pages.
Final Office Action for U.S. Appl. No. 13/082,183, filed Apr. 7, 2011 on behalf of Yue Shen et al. dated Jan. 9, 2014. 9 pages.
Final Office Action for U.S. Appl. No. 13/112,725, filed May 20, 2011 on behalf of June L. Round. dated Jan. 7, 2015. 15 pages.
Final Office Action for U.S. Appl. No. 13/112,725, filed May 20, 2011 on behalf of June L. Round. dated Oct. 24, 2013. 8 pages.
Final Office Action for U.S. Appl. No. 13/360,702, filed Jan. 28, 2012 on behalf of Sarkis K. Mazmanian et al. dated Dec. 3, 2013. 14 pages.
Final Office Action for U.S. Appl. No. 13/464,876, filed May 4, 2012 on behalf of Sarkis K. Mazmanian et al. dated Feb. 20, 2014. 20 pages.
Final Office Action for U.S. Appl. No. 13/573,695, filed Oct. 3, 2012 on behalf of Sarkis K. Mazmanian et al. dated Jan. 28, 2014. 12 pages.
Finberg et al., Decay-accelerating factor expression on either effector or target cells inhibits cytotoxicity by human natural killer cells. J Immunol. Sep. 15, 1992;149(6):2055-60.
Fink, et al. "Human antigen-presenting cells respond differently to gut-derived probiotic bacteria but mediate similar strain-dependent NK and T cell activation" FEMS Immunology and Medical Microbiology, 2007, vol. 51, No. 3; pp. 535-546.
Fontenot, J.D., et al. (2003). Foxp3 programs the development and function of CD4+CD251 + regulatory T cells. Nat Immunol 4, 330-336.
Fournier et al., Isolation of type 5 capsular polysaccharide from *Staphylococcus aureus*. Ann Inst Pasteur Microbial. Sep.-Oct. 1987;138(5):561-7.
Fridkis-Hareli et al., Binding motifs of copolymer 1 to multiple sclerosis- and rheumatoid arthritis-associated HLA-DR molecules. J Immunol. Apr. 15, 1999;162(8):4697-704.
Fridkis-Hareli et al., Binding of random copolymers of three amino acids to class 11 MHC molecules. Int Immunol. May 1999;11(5):635-41.
Fridkis-Hareli et al., Direct binding of myelin basic protein and synthetic copolymer 1 to class 11 major histocompatibility complex molecules on living antigen-presenting cells—specificity and promiscuity. Proc Natl Acad Sci USA. May 24, 1994;91(11):4872-6.
Fridkis-Hareli et al., Synthetic copolymer 1 and myelin basic protein do not require processing prior to binding to class 11 major histocompatibility complex molecules on living antigen-presenting cells. Cell Immunol. Jul. 1995;163(2):229-36.
Froicu, M. et al. "A crucial role for the vitamin D receptor in experimental inflammatory bowel diseases" Mol. Endocrinol, 2003. 17(12) oo.2386-2392.
Froicu, M., et al. Vitamin D receptor is required to control gastrointestinal immunity in IL-10 knockout mice. Immunology, 2006. 117(3) p. 310-8.
Gaboriau-Routhiau, V. et al. "The key role of segmented filamentous bacteria in the coordinated maturation of gut helper T cell responses" Immunity; vol. 31; pp. 677-689; 2009.
Gally DL et al. Environmental regulation of the fim switch controlling type 1 fimbrial phase variation in *Escherichia coli* K-12: effects of temperature and media. (1993) J Bacteriol 175:6186-93.
Garrett et al., "Colitis-Associated Colorectal Cancer Driven by T-bet Deficiency in Dendritic Cells," Cancer Cell, vol. 16, 208-19 (2009).
Garrett et al., "Enterobacteriaceae Act in Concert with the Gut Microbiota to Induce Spontaneous and Maternally Transmitted Colitis," Cell Host Microbe, vol. 8, 292-300 (2010).
Gelu-Simeon, et al., Evaluation and predictive factors of thyroid disorder due to interferon alpha in the treatment of hepatitis C. World J Gastroenterol 2009; 15(3):328-333.
GenBank Accession No. AJ277832; Hutloff Jan. 19, 2001.
GenBank Accession No. CAC06612; Hutloff Jan. 19, 2001.
GenBank Accession No. NM012092; Dec. 20, 2003.
GenBank Accession No. NP036224; Dec. 20, 2003.
Gibson 111 et al., The capsular polysaccharide complex of Bacteroides fragilis induces cytokine production from human and murine phagocytic cells. Infect Immun. Mar. 1996;64(3): pp. 1065-1069.

(56) References Cited

OTHER PUBLICATIONS

Gibson et al., "Chapter 5: trans-Galactooligosaccharides as Prebiotics". Handbook of Functional Dairy Products. Edited by Colette Shortt and John O'Brien. Published by CRC Press. 2004. 18 pages.
Glazebrook et al., A novel exopolysaccharide can function in place of the calcofluor-binding exopolysaccharide in nodulation of alfalfa by Rhizobium meliloti. Cell. Feb. 24, 1989;56(4):661-672.
Golgher et al., Galactofuranose-containing glycoconjugates of epimastigote and trypomastigote forms of Trypanosoma cruzi. Mol Biochem Parasitol. Aug. 1993;60(2):249-64.
Gondek, D.C., et al. (2005). Cutting edge: contact-mediated suppression by CD4+CD25+ regulatory cells involves a granzyme B-dependent, perforin-independent mechanism. J. Immunol.; vol. 174, 1783-1786.
Gonzalez-Hernandez et al., Peripheral blood CD161 + T cells from asthmatic patients are activated during asthma attack and predominantly produce IFN-gamma. Scand J Immunol. Apr. 2007; 65( 4):368-75.
Goverman J (2009) Autoimmune T cell responses in the central nervous system. Nat Rev Immunol 9: 393-407.
Goverman J, et al. (1993) Transgenic mice that express a myelin basic protein-specific T cell receptor develop spontaneous autoimmunity. Cell 72: 551-560.
Grabow, Bacteriophages: Update on application as models for viruses in water. Water SA 2001; 27(2):251-268.
Grivennikov et al., "IL-6 and Stat3 Are Required for Survival of Intestinal Epithelial Cells and Development of Colitis-Associated Cancer," Cancer Cell, vol. 15, 103-113 (2009).
Groux et al., Type I T-regulatory cells: their role in the control of immune responses. Transplantation. May 15, 2003;75(9 Suppl):8S-12S.
Hafter et al., Anti-CD4 and anti-CD2 monoclonal antibody infusions in subjects with multiple sclerosis. Immunosuppressive effects and human anti-mouse responses. J Immunol. Jul. 1, 1988;141(1):131-8.
Hall, J.A., et al. (2008). Commensal DNA limits regulatory T cell conversion and is a natural adjuvant of intestinal immune responses. Immunity 29, 637-649.
Hamelmann et al., Noninvasive measurement of airway responsiveness in allergic mice using barometric plethysmography. Am J Respir Crit Care Med. Sep. 1997;156(3 Pt 1):766-75.
Hampe, J., et al. (2001). Association between insertion mutation in NOD2 gene and Crohn's disease in German and British populations. Lancet 357. 1925-1928.
Hampe, J., et al. (2007). A genome-wide association scan of nonsynonymous SNPs identifies a susceptibility variant for Crohn disease in ATG 16L 1. Nat Genet 39, 207-211.
Haregewoin et al., Human gamma delta+ T cells respond to mycobacterial heat-shock protein.Nature. Jul. 27, 1989;340(6231):309-12.
Harth et al. Treatment of mycobacterium tuberculosis with antisense oligonucleotides to glutamine synthetase mRNA inhibits glutamine synthetase activity, formation of poly-L glutamate/glutamine cell wall structure, and bacterial replication. Proc Natl. Acad. Sci. 97: 418-423, 2000.
He, B., et al. (2007). Intestinal bacteria trigger T cell-independent immunoglobulin A(2) class switching by inducing epithelial-cell secretion of the cytokine April. Immunity 26, 812-826.
Hertl et al., T cell control in autoimmune bullous skin disorders. J Clin Investi. May 2006; 116(5): 1159-66. Review.
Hewison M, et al. (2003) Differential regulation of vitamin D receptor and its ligand in human monocyte-derived dendritic cells. J Immunol 170: 5382-5390.
Hirata et al., Cytokine synthesis of human monocytes stimulated by triple or single helical conformer of an antitumour (1->3)-beta-D-glucan preparation, sonifilan. Zentralbl Bakteriol. Nov. 1998;288(3):403-13.
Hodge et al., *Allium sativum* (garlic) suppresses leukocyte inflammatory cytokine production in vitro: potential therapeutic use in the treatment of inflammatory bowel disease. Cytometry. Aug. 1, 2002;48(4):209-15.
Hofstetter et al., Th17 Cells in MS and Experimental Autoimmune Encephalomyelitis. Int MS J. Apr. 2009;16(1):12-8.
Hooper, L.V. (2009). Do symbiotic bacteria subvert host immunity? Nat Rev Microbiol 7, 367-374.
Hooper, L.V. et al. (2001) Commensal host-bacterial relationships in the gut. Science 292, 1115-1118.
Hori, S. et al. "Control of regulatory T cell development by the transcription factor Foxp3" Science vol. 299, No. 5609 pp. 1057-1061 (2003).
Hu et al., "Inflammation-induced tumorigenesis in the colon is regulated by caspase-1 and NLRC4," Proc. Natl. Acad. Sci., vol. 107, 21635-21640 (2010).
Huibregtse et al., Immunopathogenesis of IBD: insufficient suppressor function in the gut? Gut. Apr. 2007;56(4):584-92. Epub Oct. 17, 2006.
Hutloff et al., ICOS is an inducible T-cell co-stimulator structurally and functionally related to CD28. Nature. Jan. 21, 1999;397(6716):263-6.
International Search Report, re International Application No. PCT/US2014/37392, dated Sep. 19, 2014, in 13 pages.
Isaksson et al., Conditional DC depletion does not affect priming of encephalitogenic Th cells in EAE. Eur J Immunol. Oct. 2012;42(10):2555-63. doi: 10.1002/eji.201142239. Epub Aug. 8, 2012.
Itokazu et al., Abscess formation as a complication caused by postoperative osteomyelitis of the femur. Arch Orthop Trauma Surg. 1998;118(1-2):99-102. Review.
Itzkowitz & Harpaz, "Diagnosis and Management of Dysplasia in Patients With Inflammatory Bowel Diseases," Gastroenterology, vol. 126, 1634-1648 (2004).
Izcue, A., et al. (2009). Regulatory lymphocytes and intestinal inflammation. Annu Rev Immunol 27, 313-338.
Japanese Decision of Rejection dated Oct. 29, 2013 for Japanese application 2010-533311 filed on Apr. 23, 2010.
Japanese Notification of Reasons for Refusal dated Feb. 12, 2014 for Japanese application 2012-507451 filed on Apr. 23, 2010.
Jawad et al, "Inflammatory Bowel Disease and Colon Cancer," Recent Results Cancer Rec., vol. 185, 99-115 (2011).
Jeffery LE, et al. (2009) 1,25-Dihydroxyvitamin D3 and IL-2 combine to inhibit T cell production of inflammatory cytokines and promote development of regulatory T cells expressing CTLA-4 and FoxP3. J Immunol 183: 5458-5467.
Jennings et al., Immunochemistry of groups A, B, and C meningococcal polysaccharide-tetanus toxoid conjugates. J Immunol. Sep. 1981;127(3): 1011-8.
Jennings et al., Induction of meningococcal group B polysaccharide-specific IgG antibodies in mice by using an N-propionylated B polysaccharide-tetanus toxoid conjugate vaccine. J Immunol. Sep. 1, 1986;137(5):1708-13.
Jia et al., Gut microbiota: a potential new territory for drug targeting. Nat Rev Drug Discov. Feb. 2008;7(2):123-9. doi: 10.1038/nrd2505.
Johnson et al., Bacterial capsular polysaccharide prevents the onset of asthma through T-cell activation. Glycobiology. Apr. 2015;25(4):368-75. doi: 10.1093/glycob/cwul 17. Epub Oct. 27, 2014.
Jonuleit et al., Identification and functional characterization of human CD4(+)CD25(+) T cells with regulatory properties isolated from peripheral blood. J Exp Med. Jun. 4, 2001 ;193(11):1285-94.
Jonuleit et al., The regulatory T cell family: distinct subsets and their interrelations. J Immunol. Dec. 15, 2003;171(12):6323-7.
Joshi S, et al. (2011) 1,25-dihydroxyvitamin 0(3) ameliorates Th17 autoimmunity via transcriptional modulation of interleukin-17A. Molecular and cellular biology 31: 3653-3669.
Jotwani et al., Pathogenicity of Bacteroides fragilis group in rat intra-abdominal abscesses. Microbial Immunol. 1992;36(10):1041-9.
Kakalacheva K, et al. (2011) Environmental triggers of multiple sclerosis. FEBS letters 585: 3724-3729.
Kalka-Moll et al., "Effect of Molecular Size on the Ability of Zwitterionic Polysaccharides to Stimulate Cellular Immunity," J. Immunol., vol. 164, 719-24 (2000).
Kalka-Moll et al., Bacteriodes Fragilis NCTC 9343 Capsular Polysaccharide PS A and the Effect of Chain Length of T cell Prolif-

(56) References Cited

OTHER PUBLICATIONS eration. Abstracts of the 98th Gen Mtg of the American Soc for Microbial. 1998; 98:123. Abstract B-405.
Kalka-Moll et al., Immunochemical and biological characterization of three capsular polysaccharides from a single Bacteroides fragilis strain. Infect Immun. Apr. 2001; 69(4):2339-44.
Kasper et al., Capsular polysaccharides and lipopolysaccharides from two Bacteroides fragilis reference strains: chemical and immunochemical characterization. J Bacterial. Feb. 1983; 153(2):991-7.
Kasper et al., Protective efficacy of immunization with capsular antigen against experimental infection with Bacteroides fragilis. J Infect Dis. Nov. 1979; 140(5):724-3 I.
Kasper et al., Surface antigens as virulence factors in infection with Bacteroides fragilis. Rev Infect Dis. Mar.-Apr. 1979;1(2):278-90.
Kasper et al., The polysaccharide capsule of Bacteroides fragilis subspecies fragilis: immunochemical and morphologic definition. J Infect Dis. Jan. 1976;133(1):79-87.
Kato et al., Interleukin 10 reduces mortality from severe peritonitis in mice. Antimicrob Agents Chemother. Jun. 1995;39(6):1336-40.
Kennedy et al., Prevention of experimental postoperative peritoneal adhesions by N,0-carboxymethyl chitosan. Surgery. Nov. 1996;120(5):866-70.
Kernodle et al. Expression of an antisense hla fragment in *Staphylococcus aureus* reduces alpha-toxin production in vitro and attenuates lethal activity in a murine model. Infection and Immunity 179-184. 1997.
Keuhn et al. "Bacterial outer membrane vesicles and the host-pathogen interaction" Genes and development; vol. 19; No. 22; Jan. 1, 2005; pp. 2645-2655.
Kidd, P. Th1/Th2 Balance: The hypothesis, its limitations, and implications for health and disease. Alternative Medicine Review 2003, 8: 223-246.
Kim, J.M., et al. (2007). Regulatory T cells prevent catastrophic autoimmunity throughout the lifespan of mice. Nat Immunol 6, 191-197.
Kinoshita et al., Retinoic acid reduces autoimmune renal injury and increases survival in NZB/W FI mice. J Immunol. Jun. 1, 2003;170(11):5793-8.
Knetsch et al., Polymers with tunable toxicity: a reference scale for cytotoxicity testing of biomaterial surfaces. J Biomed Mater Res A. Sep. 15, 2007;82(4):947-57.
Knirel et al., Somatic antigens of Pseudomonas aeruginosa. The structure of O-specific polysaccharide chains of lipopolysaccharides of P. aeruginosa 03 (Lanyi), O25 (Wokatsch) and Fisher immunotypes 3 and 7. Eur J Biochem. Sep. 15, 1987;167(3):549-61.
Knirel et al., the structure of O-specific polysaccharides and serological classification of Pseudomonas aeruginosa (a review). Acta Microbial. Hung. 1988;35(1):3-24. Review.
Koch, M.A., et al. (2009). The transcription factor T-bet controls regulatory T cell homeostasis and function during type 1 inflammation. Nat Immunol 10, 595-602.
Kong, J., et al., Novel role of the vitamin D receptor in maintaining the integrity of the intestinal mucosal barrier. Am J Physiol Gastrointest Liver Physiol, 2008. 294(1):p. G208-16.
Krause et al., An Inhibitor of Cell Proliferation Associated with Adhesion Formation Is Suppressed by N,0-Carboxymethyl Chitosan. J Investi Surg. 1988; 11:105-113.
Krutzik SR, et al. (2008) "IL-15 links TLR2/1-induced macrophage differentiation to the vitamin D-dependent antimicrobial pathway". J Immunol 181: 7115-7120.
Kuehn, M.J. et al. "Bacterial outer membrane vesicles and the host-pathogen interaction" Genes and Development vol. 19, No. 22 pp. 2645-2655 (2005).
Kuhn, R., et al. "Interleukin-10-deficient mice develop chronic enterocolitis" Cell 75, 263-74 (1993).
Kulicke et al., Correlation between immunological activity, molar mass, and molecular structure of different (1->3)-beta-D-glucans. Carbohydr Res. Jan. 2, 1997;297(2):135-43.

Kullberg, M. C. et al. Bacteria-triggered CD4(+) T regulatory cells suppress Helicobacter hepaticus-induced colitis. J Exp Med 2002, 196: 505-515.
Kullberg, M. C. et al. Induction of colitis by a CD4+ T cell clone specific for a bacterial epitope. Proc Natl Acad Sci USA 100, 15830-5 (2003).
Kuper et al., "Infections as a major preventable cause of human cancer," J. Intern. Med., vol. 248, 171-183 (2000).
Kurup et al., Antibody response to low-molecular-weight antigens of Aspergillus fumigatus in allergic bronchopulmonary aspergillosis. J Clin Microbial. Jun. 1989;27(6):1312-6.
Lagishetty, V. et al. "Vitamin D deficiency in mice impairs colonic antibacterial activity and predisposes to colitis." Endocrinology.; Jun. 2010; vol. 151(6) pp. 2423-2432.
Lee et al., "bacterial colonization factors control specificity and stability of the gut microbiota," Nature, vol. 501, 426-429 (2013).
Lee et al., Effects of in Vitro and in Vivo and Growth Conditions on Expression of Type 8 Capsular Polysaccharide by *Staphylococcus aureus*, Infection and Immunity, 61: 1853-1858, 1993.
Lee YK, et al. (2010) Has the microbiota played a critical role in the evolution of the adaptive immune system? Science 330: 1768-1773.
Lee YK, et al. (2011) Proinflammatory T-cell responses to gut microbiota promote experimental autoimmune encephalomyelitis. Proc Natl Acad Sci U S A 108 Suppl 1: 4615-4622.
Ley et al., Evolution of mammals and their gut microbes. Science. Jun. 20, 2008;320(5883): 1647-51. doi: 10.1 126/science.1155725. Epub May 22, 2008.
Lindberg et al., Virulence factors in infections with bacteroides fragilis: isolation and characterization of capsular polysaccharide and lipopolysaccharide. Scand J Infect Dis Suppl. 1982; 35:45-52.
Liu PT, et al. (2006) Toll-like receptor triggering of a vitamin D-mediated human antimicrobial response. Science 311: 1770-1773.
Liu, N. et al. "Altered endocrine and autocrine metabolism of vitamin D in a mouse model of gastrointestinal inflammation." Endocrinology, 2008; 149(10): pp. 4799-4808.
Isaksson M, et al. (2012) "Conditional DC depletion does not affect priming of encephalitogenic Th cells in EAE". Eur. J. Immunol.; 2012; vol. 42; pp. 2555-2563.
Ishikawa, H. et al., "Effect of intestinal microbiota on the induction of regulatory CD25 CD4+ T+ cells" Clin Exp Immunol 153, 127-135 (2008).
Itzkowitz et al., "Diagnosis and Management of Dysplasia in Patients With Inflammatory Bowel Diseases," Gastroenterology, vol. 126, 1634-1648 (2004).
Ivanov, 11, et al. (2008) Specific microbiota direct the differentiation of IL-17-producting T-helper cells in the mucosa of the small intestine. Cell Host Microbe 4: 337-349.
Ivanov, 11, et al. (2009) Induction of intestinal Th17 cells by segmented filamentous bacteria. Cell 139: 485-498.
Ivanov, 11, et al. Transcriptional regulation of Th17 cell differentiation. Semin Immunol, vol. 19, pp. 409-417 (2007).
Ivanov, 11. Et al. "The Orphan Nuclear Receptor RORyt Directs the Differentiation Program of Proinflammatory IL-17+ T Helper Cells" Cell 126; 1121-1133 (2006).
Lysnyansky et al. Juxtaposition of an active promoter to via genes via site-specific DNA inversions generates antigenic variation in Mycoplasma bovis. (2001) J Bacteriol 183:5698-5708.
Macpherson et al., IgA responses in the intestinal mucosa against pathogenic and nonpathogenic microorganisms. Microbes Infect. Oct. 2001;3(12):1021-35.
Macpherson et al., Interactions between commensal intestinal bacteria and the immune system. Nat Rev Immunol. Jun. 2004;4(6):478-85.
Macpherson et al., Mucosal antibodies in inflammatory bowel disease are directed against intestinal bacteria. Gut. Mar. 1996;38(3):365-75.
Macpherson, A.J .et al. (2004). Induction of protective IgA by intestinal dendritic cells carrying commensal bacteria. Science 303, 1662-1665.
Maier, B.R., et al. (1972). Experimental Shigella infections in laboratory animals. I. Antagonism by human normal flora components in gnotobiotic mice. Infect Immun 6, 168-173.

(56) References Cited

OTHER PUBLICATIONS

Makela et al., IL-10 is necessary for the expression of airway hyperresponsiveness but not pulmonary inflammation after allergic sensitization. Proc Natl Acad Sci USA. May 23, 2000;97(11):6007-12.
Mamessier et al., "Cytokines in atopic diseases: revisiting the Th2 dogma" Eur J Dermatol. Mar.-Apr. 2006; 16(2):103-113.
Mantovani et al., "Cancer-related inflammation," Nature, vol. 454, 436-444 (2008).
Maynard CL, et al. (2009) Contrasting roles for all-trans retinoic acid in TGF-beta-mediated induction of Foxp3 and IL10 genes in developing regulatory T cells. The Journal of experimental medicine 206: 343-357.
Maynard, C.L., et al. (2007). Regulatory T cells expressing interleukin 10 develop from Foxp3+ and Foxp3-precursor cells in the absence of interleukin 10. Nat Immunol 8, 931941.
Maynard, C.L., et al. Diversity in the contribution of interleukin-10 to T-cell-mediated immune regulation. Immunol. Rev., vol. 226, pp. 219-233 (2008).
Mayne CG, et al. (2011) "1,25-Dihydroxyvitamin D3 acts directly on the T lymphocyte vitamin D receptor to inhibit experimental autoimmune encephalomyelitis". European journal of immunology 41: 822-832.
Mazmanian et al. "A microbial symbiosis factor prevents intestinal inflammatory disease," Nature, vol. 453, 620-625 (2008).
Mazmanian et al., "An Immunomodulatory Molecule of Symbiotic Bacteria Directs Maturation of the Host Immune System," Cell, vol. 122, 107-118 (2005).
Mazmanian et al., Capsular polysaccharides of symbiotic bacteria modulate immune responses during experimental colitis. J Pediatr Gastroenterol Nutr. Apr. 2008;46 Suppl 1:E11-2. doi: 10.1097/01.mpg.0000313824.70971.a7.
Mazmanian, S.K. Host-bacterial symbiosis prevents intestinal inflammatory disease. California Institute of Technology. Amgen (Jul. 2008).
Mcclain et al. Inversion-independent phase variation of type 1 fimbriae in *Escherichia coli*. (1993) J. Bacteriol 175(14):4335-44.
McMurchy A.N., et al. (2012) Suppression assays with human T regulatory cells: a technical guide. European journal of immunology 42: 27-34.
Meisel-Mikolajczyk et al., Human T cell adhesion to endothelium stimulated by membrane components extracted from strains of Bacteroides vulgatus (member of B. fragilis group). Arch Immunol Ther Exp (Warsz). 1993;41 (2):129-31.
Merriam-Webster. Hypothesize. 2013. Web http://www.merriam-webster.com/dictionary/hypothesize.
Mertens, J., et al., *Streptococcus pneumoniae* Serotype 1 Capsular Polysaccharide Induces CD8+CD28− Regulatory T Lymphocytes by TCR Crosslinking, PLOS Pathogens, (Sep. 2009) vol. 5, Issue 9, e1000596, p. 1-15.
Miller et al., Severe asthma and the omalizumab option. Clinical and Molecular Allergy 2008, 6:4.
Min, B., et al. (2007). Gut flora antigens are not important in the maintenance of regulatory T cell heterogeneity and homeostasis. Eur. J. Immunol. 37; pp. 1816-1923.
Mojtabavi et al., Long-lived Th2 memory in experimental allergic asthma. J Immunol. Nov. 1, 2002;169(9):4 788-96.
Montz et al., Interleukin 10: ability to minimize postoperative intraperitoneal adhesion formation in a murine model. Fertil Steril. Jun. 1994;61(6):1136-40.
Moore, The List Goes on, New Additions to the Autoimmune Disease Raster. http://autoimmunedisease.suitel0l.com/blog.cfm/the list goes on. pp. 1-3. Aug. 7, 2007.
Moorman et al., National Surveillance of Asthma: United States, 2001-2010. National Center for Health Statistics. Vital Health Stat. 2012;3(35) 67 pages.
Mor et al., Identification of aldolase as a target antigen in Alzheimer's disease. J Immunol. Sep. 1, 2005 ;175(5):3439-45.

Mora et al., Generation of gut-homing IgA-secreting B cells by intestinal dendritic cells. Science. Nov. 17, 2206;314(5802):1157-60.
Mora et al., Selective imprinting of gut-homing T cells by Peyer's patch dendritic cells. Nature. Jul. 3, 2003;424(6944):88-93.
Morales-Tirado V, et al. (2011) 1alpha,25-dihydroxyvitamin D3 (vitamin D3) catalyzes suppressive activity on human natural regulatory T cells, uniquely modulates cell cycle progression, and augments FOXP3. Clinical immunology 138: 212-221.
Motta, A.C. et al. (2006) T cells in asthma: Lessons from mouse models. Drug Discovery Today: Disease Models, vol. 3, No. 3; pp. 199-204.
Mulholland et al., Strategies for the control of pneumococcal diseases. Vaccine. Jul. 30, 1999;17 Suppl I:S79-84. Review.
Nakayama-Imaohji, H. et al. "Identification of the site-specific DNA invertase responsible for the phase variation of SusC/SusD family outer membrane proteins in Bacteroides fragilis" J. Bacteriol.; 2009; vol. 191; No. 19; pp. 6003-6011.
Natori et al., Agelasphins, novel antitumor and immunostimulatory cerebrosides from the marine sponge *Agelas mauritianus*. Tetrahedron. 1994;50(9):2771-2784.
NCBI Sequence View "Toxin" [*Salmonella typhimurium* LT2]. Retrieved Aug. 16, 2007 from http://www.ncbi.nim.nih.oov/entrez/viewer.fcoi?db=protein&id= 17233414, pp. 1-2.
Neurath M, et al. "TNBS-colitis". Int Rev Immunol 2000, 19(1): 51-62.
Nielsen et al., Applications of peptide nucleic acids. Curr Opin Biotechnol. Feb. 1999;10(1):71-5. Review.
Niess J.H., et al. Commensal gut flora drives the expansion of proinflammatory CD4 T cells in the colonic lamina propria under normal and inflammatory conditions. J Immunol., vol. 180, Issue 1, pp. 559-568 (2008).
No Author Listed, Acute Respiratory Disease Syndrome: What is acute respiratory disease syndrome? American Lung Association. 3 pages. http://www.lungusa.org/site/apps/nlnet/content3.aspx?c=dvLUK900E&b=2058817&content. Sep. 24, 2008.
No Author Listed, Excerpts from Immunobiology, in ed. "Chapter 9. pp. 335-361; Chapter 1. pp. 2-9; Chapter 15. pp. 622-631" 2008.
No Author Listed, Lupus study. Meet a Lupus Researcher. www.lupusstudy.org/updates.php. Nov. 2005;1-2.
No Author Listed, Polyethylene Glycols (PEGs). Accessed Mar. 7, 2005. 1 page. http://www.mindfully.org/Plastic/Polymers/Polyethylene-Glycols-PEGs.htm
No Author Listed, The Merck Index. Eleventh Edition 1989:734-735.
No Author Listed, VAXA, Systemic lupus erythematosus (SLE), damaging and unpredictable. http://www.vaxa.com/arthritis-systemic-lupus-erythematosus.cfm. 1 page. Accessed Apr. 3, 2008.
Non-Final Office Action for U.S. Appl. No. 12/267,602, filed Nov. 9, 2008 on behalf of Sarkis K. Mazmanian et al. dated Jul. 15, 2011. 12 pages.
Non-Final Office Action for U.S. Appl. No. 12/766,787, filed Apr. 23, 2010 on behalf of June L. Round et al. dated Jan. 20, 2015. 18 pages.
Non-Final Office Action for U.S. Appl. No. 12/766,787, filed Apr. 23, 2010 on behalf of June L. Round et al. dated May 8, 2012. 9 pages.
Non-Final Office Action for U.S. Appl. No. 12/766,787, filed Apr. 23, 2010 on behalf of June L. Round et al. dated Sep. 30, 2013. 19 pages.
Non-Final Office Action for U.S. Appl. No. 12/831,131, filed Jul. 6, 2010 on behalf of June L. Round et al. dated Aug. 26, 2014. 20 pages.
Non-Final Office Action for U.S. Appl. No. 12/831,131, filed Jul. 6, 2010 on behalf of June L. Round et al. dated Nov. 15, 2012. 22 pages.
Non-Final Office Action for U.S. Appl. No. 13/082,183, filed Apr. 7, 2011 on behalf of Yue Shen et al. dated Aug. 13, 2013. 7 pages.
Non-Final Office Action for U.S. Appl. No. 13/082,183, filed Apr. 7, 2011 on behalf of Yue Shen et al. dated Jan. 20, 2015. 7 pages.
Non-Final Office Action for U.S. Appl. No. 13/112,725, filed May 20, 2011 on behalf of June L. Round, dated Mar. 18, 2016. 11 pages.

(56) References Cited

OTHER PUBLICATIONS

Non-Final Office Action for U.S. Appl. No. 13/112,725, filed May 20, 2011 on behalf of June L. Round, dated May 30, 2013. 7 pages.
Non-Final Office Action for U.S. Appl. No. 13/112,725, filed May 20, 2011 on behalf of June L. Round, dated May 8, 2014. 12 pages.
Non-Final Office Action for U.S. Appl. No. 13/360,702, filed Jan. 28, 2012 on behalf of Sarkis K. Mazmanian et al. dated Mar. 11, 2015. 13 pages.
Non-Final Office Action for U.S. Appl. No. 13/360,702, filed Jan. 28, 2012 on behalf of Sarkis K. Mazmanian et al. dated Mar. 18, 2013. 13 pages.
Non-Final Office Action for U.S. Appl. No. 13/464,876, filed May 4, 2012 on behalf of Sarkis K. Mazmanian et al. dated Jul. 9, 2013. 16 pages.
Non-Final Office Action for U.S. Appl. No. 13/573,695, filed Oct. 3, 2012 on behalf of Sarkis K. Mazmanian et al. dated Aug. 28, 2013. 11 pages.
Non-Final Office Action for U.S. Appl. No. 14/015,769, filed Aug. 30, 2013 on behalf of Sarkis K. Mazmanian et al. dated Dec. 31, 2014. 7 pages.
Norman; "Thyroiditis—Inflammation of the thyroid gland"; Endocrineweb 2009; www.endrocrineweb.com/throiditis.html, 1-4. Dowloaded Jul. 28, 2009.
Notice of Allowance for U.S. Appl. No. 13/573,695, filed Oct. 3, 2012 on behalf of Sarkis K. Mazmanian et al. dated Feb. 13, 2015. 9 pages.
Notice of Allowance for U.S. Appl. No. 13/573,695, filed Oct. 3, 2012 on behalf of Sarkis K. Mazmanian et al. dated May 15, 2015. 2 pages.
Notice of Reasons for Rejection for JP 2010-533311 dated May 14, 2013 (English Translation).
Notification of Reason for Refusal for Japanese Patent Application No. 2013-511406. dated Apr. 12, 2016. 7 pages.
Notification of Reasons for Refusal for Japanee Patent Application No. 2013-511406. dated May 12, 2015.6 pages (Japanese original+ English translation).
Noverr MC, et al. (2004) Does the microbiota regulate immune responses outside the gut? Trends Microbiol 12: 562-568.
Nylander A, et al. (2012) "Multiple sclerosis". The Journal of Clinical Investigation; vol. 122; DO. 1180-1188.
Ochoa-Reparaz J, et al. (2009) Role of gut commensal microflora in the development of experimental autoimmune encephalomyelitis. J Immunol 183: 6041-6050.
Ochoa-Reparaz J, et al. (2010) A polysaccharide from the human commensal Bacteroides fragilis protects against CNS demyelinating disease. Mucosal Immunol 3: 487-495.
Ochoa-Reparaz J, et al. (2010) Central nervous system demyelinating disease protection by the human commensal Bacteroides fragilis depends on polysaccharide A expression. J Immunol 185: 4101-4108.
Ochoa-Reparaz, J. et al. "The role of subcellular fractions of commensal bacteroides fragilis in the control of experimental autoimmune encephalomyelitis" Multiple Sclerosis; Sep. 2009; vol. 15; (Abstract Only).
O'Connor et al., Translational mini-review series on Th17 cells: CD4 T helper cells: functional plasticity and differential sensitivity to regulatory T cell-mediated regulation. Clin Exp Immunol. Feb. 2010; I59(2):137-47. doi: 10.1111/j.1365-2249.2009.04040.x. Epub Nov. 11, 2009.
Oda et al., A comprehensive map of the toll-like receptor signaling network. Mol Syst Biol. 2006;2;2006.0015. Epub Apr. 18, 2006.
Office Action for Japanese patent application No. JP2015-116494, dated Jul. 12, 2016. 8 pages. (Japanese original + English translation).
Oh et al., CD4 T-helper cells engineered to produce IL-10 prevent allergen-induced airway hyperreactivity and inflammation. J Allergy Clin Immunol. Sep. 2002;110(3):460-8.
Ohno et al., Comparison of the immunopharmacological activities of triple and single-helical schizophyllan in mice. Biol Pharm Bull. Sep. 1995;18(9):1242-7.
Ohno et al., Enhancement of LPS triggered TNF-alpha (tumor necrosis factor-alpha) production by (1->3)-beta-D-glucans in mice. Biol Pharm Bull. Jan. 1995;18(1):126-33.
Onderdonk et al., The capsular polysaccharide of Bacteroides fragilis as a virulence factor: comparison of the pathogenic potential of encapsulated and unencapsulated strains. J Infect Dis. Jul. 1977;136(1):82-9.
Onderdonk, A. et al., Evidence for T Cell-dependent Immunity to Bacteroides fragilis in an Intraabdominal Abscess Model; J. Clin Investi. 69:9-16 (1982).
Ostman, S., et al., Impaired regulatory T cell function in germ-free mice, European Journal of Immunology 2006, 36: 2336-2346.
Ozenci et al., Multiple sclerosis: levels of interleukin-10-secreting blood mononuclear cells are low in untreated patients but augmented during interferon-beta-1 b treatment. Scand J Immunol. May 1999;49(5):554-61.
Palmer MT, et al. (2011) Lineage-specific effects of 1,25-dihydroxyvitamin D(3) on the development of effector CD4 T cells. The Journal of biological chemistry 286: 997-1004.
Pantosti et al., Bacteroides fragilis strains express multiple capsular polysaccharides. J Clin Microbial. Jul. 1993;31(7):1850-5.
Paoletti et al., Effects of chain length on the immunogenicity in rabbits of group B *Streptococcus* type 111 oligosaccharide-tetanus toxoid conjugates. J Clin Investi. Jan. 1992;89(1):203-9.
Paoletti et al., Neonatal Mouse Protection against Infection with Multiple Group B Streptococcal (GBS) Serotypes by Maternal Immunization with a Tetravalent GBS Polysaccharide-Tetanus Toxoid Conjugate Vaccine, Infection and Immunity, 62:3236-3243, 1994.
Park et al., Interleukin-2 and soluble interleukin-2 receptor in bronchoalveolar lavage fluid from patients with bronchial asthma. Chest. Aug. 1994;106(2):400-6.
Patrick et al. "Mutational analysis of genes implicated in LPS and capsular polysaccharide biosynthesis in the opportunistic pathogen Bacteroides fragilis" Microbiology. Apr. 2009;155(Pt 4):1039-49.
Patrick, S., et al., A comparison of the haemagglutinating and enzymic activities of Bacteroides fragilis whole cells and outer membrane vesicles, Microbial Pathogenesis 1996, 20: 191-202.
Pavliak et al., Structural elucidation of the capsular polysaccharide of Bacteroides fragilis strain 23745MI. Carbohydr Res. Oct. 2, 1995;275(2):333-41.
PCT International Search Report and Written Opinion for International Patent Application No. PCT/US2012/023050, dated May 21, 2012. 7 pages.
PCT International Search Report and Written Opinion for International Patent Application No. PCT/US2014/37392, dated Sep. 19, 2014. 13 pages.
PCT International Search Report and Written Opinion for PCT Application No. PCT/US2014/037392 filed May 8, 2014, dated Sep. 19, 2014. 28 pages.
PCT International Search Report for PCT/US2008/082928 filed Nov. 9, 2008, dated Jun. 30, 2009. 5 pages.
PCT International Search Report for PCT/US2010/032300 filed Apr. 23, 2010, dated Jan. 31, 2011. 5 pages.
PCT Written Opinion for PCT/US2010/032300 filed Apr. 23, 2010, dated Jan. 31, 2011. 5 pages.
PCT Written Opinion dated Jun. 30, 2009 for PCT/US2008/082928 filed on Nov. 9, 2008.
Pedersen LB, et al. (2007) 1,25-dihydroxyvitamin D3 reverses experimental autoimmune encephalomyelitis by inhibiting chemokine synthesis and monocyte trafficking. J Neurosci Res 85: 2480-2490.
Perumal et al., Protective effect of interleukin-2 on experimental intra-abdominal abscess development due to Bacteriodes Fragilis. Clinical Research. 1990;38(2):550A.
Pierrot-Deseilligny C, et al. Is hypovitaminosis Done of the environmental risk factors for multiple sclerosis? Brain; 2010; 133: 1869-1888.
Popivanova et al., "Blocking TNF-a in mice reduces colorectal carcinogenesis associated with chronic colitis," J. Clin. Invest., vol. 118, 560-570 (2008).
Popovic et al., Inhibition of autoimmune encephalomyelitis by a tetracycline. Ann Neural. Feb. 2002;51(2):215-23.

(56) References Cited

OTHER PUBLICATIONS

Power C, et al. (2010) The human microbiome in multiple sclerosis: pathogenic or protective constituents? The Canadian journal of neurological sciences Le journal canadien des sciences neurologiques 37 Suppl 2: S24-33.
Poxton et al., Mucosa-associated bacterial flora of the human colon. J Med Microbial. Jan. 1997;46(1):85-91.
Prieto et al., A new ganglioside in human meconium detected by antiserum against the human milk sialyloligosaccharide, LS-tetrasaccharide b, Archives of Biochemistry and Biophysics, 241:281-289, 1985.
Rabe et al., Pharmacological treatment of asthma today. Eur Respir J Suppl. 2001; 34:34s-40s.
Raetz et al., Lipopolysaccharide endotoxins. Annu Rev Biochem. 2002;71 :635-700. Epub Nov. 9, 2001.
Raghuwanshi, A. et al. "Vitamin D and Multiple Sclerosis" Journal of Cellular Biochemistry; 2008; vol. 105; pp. 338-343.
Raman et al. Vitamin D and gastrointestinal diseases: inflammatory bowel disease and colorectal cancer in Ther Adv. Gastroenterology, Jan. 10, 2011 (Jan. 10, 2011) vol. 4, pp. 49-62.
Ranua et al., Serum IgA, IgG, and IgM concentrations in patients with epilepsy and matched controls: a cohort-based cross-sectional study. Epilepsy Behav. Mar. 2005; 6(2):191-5.
Rescigno, M. et al., "Dendritic cells express tight junction proteins and penetrate gut epithelial monolayers to sample bacteria" Nat Immunol 2, 361 (2001).
Restriction Requirement for U.S. Appl. No. 12/267,602, filed Nov. 9, 2008 on behalf of Sarkis K. Mazmanian et al. dated Mar. 17, 2011. 9 pages.
Restriction Requirement for U.S. Appl. No. 12/766,787, filed Apr. 23, 2010 on behalf of June L. Round et al. dated Mar. 15, 2012. 9 pages.
Restriction Requirement for U.S. Appl. No. 12/831,131, filed Jul. 6, 2010 on behalf of June L. Round et al. dated Jul. 11, 2012. 9 pages.
Restriction Requirement for U.S. Appl. No. 13/082,183, filed Apr. 7, 2011 on behalf of Yue Shen et al. dated May 31, 2013. 7 pages.
Restriction Requirement for U.S. Appl. No. 13/112,725, filed May 20, 2011 on behalf of June L. Round, dated Mar. 18, 2013. 7 pages.
Restriction Requirement for U.S. Appl. No. 13/360,702, filed Jan. 28, 2012 on behalf of Sarkis K. Mazmanian et al. dated Feb. 1, 2013. 6 pages.
Restriction Requirement for U.S. Appl. No. 13/464,876, filed May 4, 2012 on behalf of Sarkis K. Mazmanian et al. dated Feb. 20, 2013. 7 pages.
Restriction Requirement for U.S. Appl. No. 13/573,695, filed Oct. 3, 2012 on behalf of Sarkis K. Mazmanian et al. dated May 23, 2013. 9 pages.
Restriction Requirement for U.S. Appl. No. 14/015,769, filed Aug. 30, 2013 on behalf of Sarkis K. Mazmanian et al. dated Aug. 18, 2014. 8 pages.
Restriction Requirement for U.S. Appl. No. 14/755,327, filed Jun. 30, 2015 on behalf of Sarkis K. Mazmanian et al. dated Aug. 11, 2016. 8 pages.
Riesenfeld et al., Biosynthesis of heparin. Assay and properties of the microsomal N-acetyl-Dglucosaminyl N-deacetylase.J Biol Chem. Feb. 10, 1980;255(3):922-8.
Rodgers et al., "Prescribing an antibiotic? Pair it with probiotics", The Journal of Family Practice, Mar. 2013, pp. 148-150, vol. 62, No. 3.
Roncarolo et al., Type IT regulatory cells. Immunol Rev. Aug. 2001; 182:68-79. Review.
Round JL, et al. (2009) Coordination of tolerogenic immune responses by the commensal microbiota. J Autoimmun.
Round JL, et al. (2011) The Toll-like receptor 2 pathway establishes colonization by a commensal of the human microbiota. Science 332: 974-977.
Rubtsov, Y.P., et al. Regulatory T cell-derived interleukin-10 limits inflammation at environmental interfaces. Immunity, vol. 28, Issue 4, pp. 546-558 (2008).
Runia TF, et al. (2012) Lower serum vitamin D levels are associated with a higher relapse risk in multiple sclerosis. Neurology 79: 261-266.
Rypens et al., Percutaneous drainage of abdominal abscesses in pediatric Crohn's disease. AJR Am J Roentgenol. Feb. 2007;188(2):579-85.
Sakaguchi S, et al. (2008) Regulatory T cells and immune tolerance. Cell 133: 775-787.
Sakaguchi, S. et al. (2006) Foxp3+ CD25+ CD4+ natural regulatory T cells in dominant self-tolerance and autoimmune disease. Immunol. Rev. 212, pp. 8-27.
Salyers et al., Conjugative transposons: an unusual and diverse set of integrated gene transfer elements. Microbial Rev. Dec. 1995;59(4):579-90. Review.
Sartor, R. B. Mechanisms of disease: pathogenesis of Crohn's disease and ulcerative colitis. Nat Clin Pract Gastroenterol Hepatol 3, 390-407 (2006).
Schembri MA et al. Orientation-dependent enhancement by H-NS of the activity of the type 1 fimbrial phase switch promoter in *Escherichia coli*. (1998) Mol Gen Genet 259:336-44.
Schlegel et al., A synthetic random basic copolymer with promiscuous binding to class 11 major histocompatibility complex molecules inhibits T-cell proliferative responses to major and minor histocompatibility antigens in vitro and confers the capacity to prevent murine graft-versus-host disease in vivo. Proc Natl Acad Sci USA. May 14, 1996;93(10):5061-6. Erratum in: Proc Natl Acad Sci USA Aug. 6, 1996;93(16):8796.
Schneider et al., De nova design of molecular architectures by evolutionary assembly of drug derived building blocks. J Comput Aided Mol Des. Jul. 2000;14(5):487-94.
Segal et al., Severe insulin resistance secondary to insulin antibodies: successful treatment with the immunosuppressant MMF. Pediatr Diabetes. Jun. 2008;9(3 Pt 1):250-4.
Sellin et al., Conformational analysis of a toxic peptide from Trimeresurus wagleri which blocks the nicotinic acetylcholine receptor. Biophys J. Jan. 1996;70(1):3-13.
Shaklee et al., Hydrazinolysis of heparin and other glycosaminoglycans. Biochem. J. (1984); 217: 187-197.
Shapiro et al., Cellular control of abscess formation: role of T cells in the regulation of abscesses formed in response to Bacteroides fragilis. J Immunol. Jul. 1, 1986;137(1):341-6.
Shapiro et al., Cellular immunity to Bacteroides fragilis capsular polysaccharide. J Exp Med. Apr. 1, 1982;155(4):1188-97.
Sharpe et al., The B7-CD28 superfamily. Nat Rev Immunol. Feb. 2002;2(2): 116-26. Review.
Shevach, CD4+ CD25+ suppressor T cells: more questions than answers. Nat Rev Immunol. Jun. 2002;2(6):389-400. Review.
Sigmundsdottir H, et al. (2007) DCs metabolize sunlight-induced vitamin D3 to 'program' T cell attraction to the epidermal chemokine CCL27. Nature immunology 8: 285-293.
Silvestro et al. "Effects of subinhibitory concentrations of clindamycin on the morphological, biochemical and genetic characteristics of Bacteroides fragilis" FEMS Microbiol. Lett. 2006; vol. 257; No. 2; pp. 189-194.
Simmons et al., Synthesis and membrane permeability of PNA-peptide conjugates. Bioorg Med Chem Lett. 1997;7(23):3001-6.
Slack, E., et al. (2009). Innate and adaptive immunity cooperate flexibly to maintain host-microbiota mutualism. Science 325, 617-620.
Smith SG et al. Functional analysis of the FimE integrase of *Escherichia coli* K-12: isolation of mutant derivatives with altered DNA inversion preferences. (1999) Mol Microbiol 34:965-79.
Smits, H.H. et al. "Selective probiotic bacteria induce IL-10-producing regulatory T cells in vitro by modulating dendritic cell function through dendritic cell-specific intercellular adhesion molecule 3-grabbing nonintegrin" J Allergy Clin Immunol. (2005) pp. 1260-1267.
Solomon AJ, et al. "Multiple Sclerosis and Vitamin D: A Review and Recommendations" Curr. Neurol Neurosci Rep.; 2010; vol. 10; pp. 389-396.
Spach KM, et al. (2005) Vitamin D3 confers protection from autoimmune encephalomyelitis only in female mice. J Immunol 175: 4119-4126.

(56) References Cited

OTHER PUBLICATIONS

Spach KM, et al. (2004) Gene expression analysis suggests that 1,25-dihydroxyvitamin D3 reverses experimental autoimmune encephalomyelitis by stimulating inflammatory cell apoptosis. Physiol Genomics 18: 141-151.
Sprinz, H. et al. (1961) The response of the germfree guinea pig to oral bacterial challenge with Escherichia coli and Shigella flexneri. Am J. Pathol. 39, 681-695.
Stein et al., Thymus-independent and thymus-dependent responses to polysaccharide antigens. J Infect Dis. Jun. 1992;165 Suppl I:S49-52. Review.
Stephen et al. "Effect of 87-2 and CD40 Signals from Activated Antigen-Presenting Cells on the Ability of Zwitterionic Polysaccharides to Induce T-Cell Stimulation" 2005; Inf. Immun. vol. 73; pp. 2184-2189.
Stewart N, et al. (2012) Interferon-beta and serum 25-hydroxyvitamin D interact to modulate relapse risk in MS. Neurology 79: 254-260.
Stockinger B, Veldhoen M. Differentiation and function of Th17 T cells. Current Opinion in Immunology. 19:281-286 (2007).
Stromnes et al., Passive induction of experimental allergic encephalomyelitis. Nat Protoc. 2006; 1(4): 1952-60.
Suri-Payer et al., CD4+CD25+ T cells inhibit both the induction and effector function of autoreactive T cells and represent a unique lineage of immunoregulatory cells. J Immunol. Feb. 1, 1998; 160(3):1212-8.
Szu et al., Relation between structure and immunologic properties of the Vi capsular polysaccharide. Infect Immun. Dec. 1991;59(12):4555-61.
Takatori, N. "Probiotics, beneficial bacteria, and inflammatory bowel disease; What do we actually know?" Nutritional Bytes, 2009, vol. 13, pp. 1-6.
Tanaka, H. et al. "Human monocyte-derived dendritic cells induce naive T cell differentiation into T helper cell type 2 (Th2) of Th1/Th2 effectors: role of stimulator/responder ratio" Journal of Experimental Medicine; vol. 192; No. 3; Aug. 7, 2000; pp. 405-411.
Tang et al., Th type 1-stimulating activity of lung macrophages inhibits Th2-mediated allergic airway inflammation by an IFN-gamma-dependent mechanism. J Immunol. Feb. 1, 2001; 166(3): 1471-81.
Tang, et al. "In-vitro-expanded Antigen-specific Regulatory T cells suppress autoimmune diabetes" J. Exp. Med. vol. 199; No. 11; Jun. 7, 2004; pp. 1455-1465.
Taylor et al., Stoichiometric depolymerization of polyuronides and glycosaminoglycuronans to monosaccharides following reduction of their carbodiimide-activated carboxyl groups. Biochemistry. Apr. 11, 1972;11 (8): 1383-8.
Teitelbaum et al., Immunomodulation of experimental autoimmune encephalomyelitis by oral administration of copolymer 1. Proc Natl Acad Sci USA. Mar. 30, 1999;96(7):3842-7.
Teitelbaum et al., Specific inhibition of the T-cell response to myelin basic protein by the synthetic copolymer Cop 1. Proc Natl Acad Sci USA. Dec. 1988;85(24):9724-8.
Teitelbaum et al., Synthetic copolymer 1 inhibits human T-cell lines specific for myelin basic protein. Proc Natl Acad Sci USA. Jan. 1, 1992;89(1):137-41.
Teitelbaum et al., Unprimed spleen cell populations recognize macrophage-bound antigen with opposite net electric charge. Proc Natl Acad Sci USA. Apr. 1977;74(4):1693-6.
The Language of Prevention, National Public Health Partnership, 2006, 9 pages.
Thomas et al., Randomised controlled trial of short bursts of a potent topical corticosteroid versus prolonged use of a mild preparation for children with mild or moderate atopic eczema. BMJ. 2002;324(7640):1-7.
Tong et al., "Mouse Models of Colorectal Cancer," Chin. J. Cancer, vol. 30, 450-62 (2011).
Tournoy et al., Endogenous interleukin-10 suppresses allergen-induced airway inflammation and nonspecific airway responsiveness. Clin Exp Allergy. Jun. 2000;30(6):775-83.

Toussirot, E., et al., Bacterial extract (OM-89) specific and non specific immunomodulation in rheumatoid arthritis patients, Autoimmunity 2006, 39: 299-306 Abstract Only.
Triantafillidis et al., "Colorectal Cancer and Inflammatory Bowel Disease: Epidemiology, Risk Factors, Mechanisms of Carcinogenesis and Prevention Strategies," Anticancer Res., vol. 29, 2727-37 (2009).
Troy, E. et al. "Beneficial effects of Bacteroides fragilis polysaccharides on the immune system." Front Biosci., Jan. 1, 2010, vol. 15; pp. 25-34.
Troy, E. et al., "Orientations of the Bacteroides fragilis capsular polysaccharide biosynthesis locus promoters during symbiosis and infection", Journal of Bacteriology, Nov. 2010, vol. 192, No. 21, pp. 5832-5836.
Tzianabos et al., "The Capsular Polysaccharide of Bacteroides frugilis Comprises Two Ionically Linked Polysaccharide," J. Biol. Chem., vol. 267, 18230-5 (1992).
Tzianabos et al. "T-Cells Activated by Zwitterionic Molecules prevent abscesses induced by pathogenic bacteria" J. Biol. Chem. 2000; vol. 275; No. 10; pp. 6733-6740.
Tzianabos et al., Bacterial structure and functional relation to abscess formation. Infect Agents Dis. Oct. 1994;3(5):256-65. Review.
Tzianabos et al., Characteristics of bacterial polysaccharides that activate T cells. The International Carbohydrate Symposium XVII. Jul. 21, 1994. 1 page.
Tzianabos et al., Effect of surgical adhesion reduction devices on the propagation of experimental intra-abdominal infection. Arch Surg. Nov. 1999;134(11):1254-9.
Tzianabos et al., IL-2 mediates protection against abscess formation in an experimental model of sepsis. J Immunol.Jul. 15, 1999;163(2):893-7.
Tzianabos et al., Protection against experimental intraabdominal sepsis by two polysaccharide immunomodulators. J Infect Dis. Jul. 1998;178(1):200-6.
Tzianabos et al., Structure-function relationships for polysaccharide-induced intra-abdominal abscesses. Infect Immun. Aug. 1994;62(8):3590-3.
Tzianabos et al., T Cell Activation by Zwitterionic polysaccharides and peptide mimetics prevents intrabdominal abscess formation. Abstracts of the 99th General Meeting of the American Society for Microbiology. Chicago, US: May 30-Jun. 3, 1999. Jun. 28, 1999; 1 page.
Tzianabos, A.O. et al. Structural Characteristics of Polysaccharides that Induce Protection Against Intra-Abdominal Abscess Formation. Infection and Immunity, American Society for Microbiology, vol. 62, No. 11, Nov. 1, 1994, pp. 4881-4886.
Tzianabos, A.O., Polysaccharide Immunomodulators as Therapeutic Agents: Structural Aspects and Biologic Function, Clin. Microbial. Rev. 13(4):523-533 (2000).
Tzianabos, AO et al., Polysaccharide-mediated protection against abscess formation in experimental intra-abdominal sepsis. J Clin. Investi. (1995) 96:2727-31.
Tzianabos, et al., Structural rationale for the modulation of abscess formation by Staphylococcus aureus capsular polysaccharides. Proc Natl Acad Sci USA. Jul. 31, 2001 ;98(16):9365-70. Epub Jul. 24, 2001.
Uronis et al., "Modulation of the Intestinal Microbiota Alters Colitis-Associated Colorectal Cancer Susceptibility," PLoS One, vol. 4, e6026 (2009).
Van Maren, W.W.C., Toll-like receptor signalling on Tregs: to suppress or not to suppress? Immunology, vol. 124, Issue 4, pp. 445-452 (2008).
Van Scott et al., IL-10 reduces Th2 cytokine production and eosinophilia but augments airway reactivity in allergic mice. Am J Physiol Lung Cell Mol Physiol. Apr. 2000;278(4):L667-74.
Vann et al., The structure of the capsular polysaccharide (K5 antigen) of urinary-tract-infective Escherichia coli O10:K5:H4. A polymer similar to desulfo-heparin. Eur J Biochem. May 15, 1981; 116(2):359-64.
Veldhoen, M. et al. "TGF beta in the context of an inflammatory cytokine milieu supports de novo differentiation of IL-17-producing T cells." Immunity; vol. 24; pp. 179-189.

(56) References Cited

OTHER PUBLICATIONS

Velez et al., Type I *Streptococcus pneumoniae* carbohydrate utilizes a nitric oxide and MGC 11-dependent pathway for antigen presentation. Immunol. 2008; 127:73-82.
Verdu et al., Oral administration of antigens from intestinal flora anaerobic bacteria reduces the severity of experimental acute colitis in BALB/c mice. Clin Exp Immunol. Apr. 2000;120(1):46-50.
Vignali, DA et al. "How regulatory T cells work." Nat. Rev. Immunol.; 2008; vol. 8; pp. 523-532.
Vinderola et al., Effects of the oral administration of the exopolysaccharide produced by Lactobacillus kefiranofaciens on the gut mucosal immunity. Cytokine. Dec. 2006;36(5-6):254-60. Epub Mar. 23, 2007.
Viret et al., Molecular cloning and characterization of the genetic determinants that express the complete Shigella serotype D (Shigella sonnei) lipopolysaccharide in heterologous live attenuated vaccine strains. Mol Microbial. Jan. 1993;7(2):239-52.
Wagner et al., Use of reporter cells to study endogenous retinoid sources in embryonic tissues. Methods Enzymol. 1997;282:98-107.
Wang et al., "A bacterial carbohydrate links innate and adaptive responses through Toll-like receptor 2," J. Exp. Med., vol. 203, 2853-63 (2006).
Wang et al., Lipopolysaccharide: Biosynthetic pathway and structure modification. Prog Lipid Res. Apr. 2010;49(2):97-107. doi: 10.1016/j.plipres.2009.06.002. Epub Oct. 6, 2009.
Wang et al., Ozonolysis for selectively depolymerizing polysaccharides containing β-d-aldosidic linkages. Proc Natl Acad Sci USA. Jun. 9, 1998; 95(12): 6584-6589.
Wang et al., Structural basis of the abscess-modulating polysaccharide A2 from Bacteroides fragilis. Proc Natl Acad Sci USA. Dec. 5, 2000;97(25): 13478-83.
Wang et al., Structure characterization of an abscessogenic capsular polysaccharide from Bacteriodes fragilis by NMR spectroscopy. XIX International Conference of NMR in Biological Systems. Florence, Italy. Aug. 20-25, 2000. Abstract.
Ward et al., The nucleotide sequence of the tnpA gene of Tn21, Nucleic Acids Research, vol. 15(4), 1987, 1799-1806.
Wehr et al., Anti-low-density lipoprotein antibodies in alcoholics without and with liver disease and in social drinkers. Alcohol Alcohol. Jan.-Feb. 1997;32(1):43-9.
Weinacht et al. Phase variation of the capsular polysaccharides of Bacteroides fragilis is dictated by site-specific recombinases. 2002 General Meeting of the American Society for Microbiology, May 19-23, 2002. Abstract.
Wen, L. et al. "Innate immunity and intestinal microbiota in the development of Type 1 diabetes" Nature; 2008; vol. 455; pp. 1109-1113.
Wessels et al., Structural Determination and Immunochemical Characterization of the Type V Group B *Streptococcus* Capsular Polysaccharide, The Journal of Biological Chemistry, 266:6714-6719, 1991.
Wessels et al., Structure and immunochemistry of an oligosaccharide repeating unit of the capsular polysaccharide of Type 111 group B *Streptococcus*. A revised structure for the type 111 group B streptococcal polysaccharide antigen. J Biol Chem. 1987;262(17):8262-7.
Wexler, Bacteroides: the good, the bad, and the nitty-gritty. Clin Microbial Rev. Oct. 2007;20(4):593-621.
Whitfield, Biosynthesis and assembly of capsular polysaccharides in *Escherichia coli*. Annu Rev Biochem. 2006; 75:39-68.
Wiegandt et al., Carbohydrate Components of Extraneuronal Gangliosides from Bovine and Human Spleen, and Bovine Kidney, European Journal of Biochemistry, 15:287-292, 1970.
Willer CJ, et al. (2003) Twin concordance and sibling recurrence rates in multiple sclerosis. Proc Natl Acad Sci USA 100: 12877-12882.
Wirtz et al., Mouse models of inflammatory bowel disease. Adv Drug Deliv Rev. Sep. 30, 2007;59(11):1073-83. Eoub Aug. 16, 2007.
Woessner et al., Long-term antibiotic treatment with roxithromycin in patients with multiple sclerosis. Infection. Dec. 2006;34(6):342-4.
Woodruff, et al., Sudden-onset severe acute asthma: Clinical features and response to therapy, Academic Emergency Med. 1998, 5: 695-701.
Wu HJ, et al. (2010) Gut-residing segmented filamentous bacteria drive autoimmune arthritis via T helper 17 cells. Immunity 32: 815-827.
Wujek et al., A carbohydrate polymer that effectively prevents epidural fibrosis at laminectomy sites in the rat. Exp Neural. Nov. 1991;114(2):237-45.
Xie & Itzkowitz, "Cancer in inflammatory bowel disease," World J. Gastroenterol., vol. 14, 378-89 (2008).
Xu Jet al., A genomic view of the human-Bacteroides thetaiotaomicron symbiosis. Science. Mar. 28, 2003;299(5615):2074-6.
Yamakazi et al. "Dendritic cells are specialized accessory cells along with TGF-beta for the differentiation of Foxp3+ CD4+ regulatory T cells from peripheral Foxp3− precursors" Blood. 2007; 110: 4293-4302.
Yamakazi et al. (Blood. 2007; 110: Supplemental Figure SS) (http://www.bloodjournal.org/content/bloodjournal/suppl/2007/08/14/blood-2007-05-088831.DC1/FigureS5jpg).
Yamazaki et al., Dendritic cells are specialized accessory cells along with TGF—for the differentiation of Foxp3+ CD4+ regulatory T cells from peripheral Foxp3 precursors. Blood. Dec. 15, 2007;110(13):4293-302. Epub Aug. 15, 2007.
Yamazaki, T. et al. "CCR6 regulates the migration of inflammatory and regulatory T cells" J. Immunology; 2008; vol. 181; pp. 8391-8401.
Yokoyama et al., Adhesion behavior of rat lymphocytes to poly(ether)-poly(amino acid) block and graft copolymers. J Biomed Mater Res. Sep. 1986;20(7):867-78.
Yoshii, Cytotoxic effects of acrylates and methacrylates: relationships of monomer structures and cytotoxicity. J Biomed Mater Res. Dec. 15, 1997;37(4):517-24.
Zabad et al., The clinical response to minocycline in multiple sclerosis is accompanied by beneficial immune changes: a pilot study. Mult Scler. May 2007;13(4):517-26. Epub Feb. 9, 2007.
Zaleznik et al., A soluble suppressor T cell factor protects against experimental intraabdominal abscessess. J Clin Investi. Mar. 1985;75(3):1023-7.
Zaph, C., et al. (2008). Commensal-dependent expression of IL-25 regulates the IL-23-IL-17 axis in the intestine. J Exp Med 205, 2191-2198.
Zehnder D, et al. (1999) Expression of 25-hydroxyvitamin D3-1alpha-hydroxylase in the human kidney. J Am Soc Nephrol 10: 2465-2473.
Zehnder D, et al. (2001) Extrarenal expression of 25-hydroxyvitamin d(3)-1 alpha-hydroxylase. J Clin Endocrinol Metab 86: 888-894.
Zhang et al., Degradation of Wood Polysaccharide Model Compounds During Ozone Treatment. Journal of Pulp and Paper Science. Jan. 1997;23(1):J23-J27.
Zhang et al., IL-10 is involved in the suppression of experimental autoimmune encephalomyelitis by CD25+CD4+ regulatory T cells. Int Immunol. Feb. 2004;16(2):249-56.
Zhao H et al. In vivo phase variation of MR/P fimbrial gene expression in Proteus mirabilis infecting the urinary tract. (1997) Mol Micro biol 23: 1009-19.
Zhou, L. et al. "TGF-beta-induced Foxp3 inhibits T(H)17 cell differentiation by antagonizing RORgammat function" Nature; 2008; vol. 453; pp. 236-240.
Zhu et al., Oral administration of type-11 collagen peptide 250-270 suppresses specific cellular and humoral immune response in collagen-induced arthritis. Clin Immunol. Jan. 2007; 122(1):75-84. Epub Oct. 11, 2006.
Davila et al., "Efficacy and Toxicity Management of 19-28z CAR T Cell Therapy in B Cell Acute Lymphoblastic Leukemia.," Sci Transl Med. 2014, 6(224), 224ra25, 1-12. doi:10.1126/scitranslmed.3008226.
Notice of Reasons for Refusal dated Mar. 24, 2020 in Japanese Patent Application No. 2019-061261.

(56) References Cited

OTHER PUBLICATIONS

Office Action dated Feb. 18, 2020 in Canadian Patent Application No. 2,911,826.

\* cited by examiner

PROBIOTIC PREVENTION AND TREATMENT OF COLON CANCER

INCORPORATION BY REFERENCE TO ANY PRIORITY APPLICATIONS

The present application claims priority under 35 U.S.C. § 119(e) to U.S. Provisional Application No. 61/822,126, filed May 10, 2013, which is herein expressly incorporated by reference in its entirety.

STATEMENT REGARDING FEDERALLY SPONSORED R&D

This invention was made with government support under DK078938 awarded by the National Institutes of Health. The government has certain rights in the invention.

REFERENCE TO SEQUENCE LISTING

The present application is being filed along with a Sequence Listing in electronic format. The Sequence Listing is provided as a file entitled SEQLISTING.TXT, created May 9, 2014, which is 4 Kb in size. The information in the electronic format of the Sequence Listing is incorporated herein by reference in its entirety.

BACKGROUND OF THE INVENTION

Field of the Invention

The present application relates generally to the field of prevention and treatment of colorectal cancer.

Description of the Related Art

Colorectal cancer is the third most common malignancy in the world and inflammatory bowel diseases (IBD) increase the risk of colorectal cancer in humans. Although the etiology of chronic inflammation and cancer in the intestine is not yet elucidated, it is thought that it may be a result of a disruption of immune balance between proinflammatory and anti-inflammatory responses by inappropriate response to intestinal microbiota. Proinflammatory cytokines and chemokines produced during chronic intestinal inflammation may then initiate and promote colon tumorigenesis.

Colonization of mice with *Bacteroides fragilis* or oral treatment of mice with its immunomodulatory molecule polysaccharide A (PSA) has been shown to protect against the development of experimental colitis using the well-established CD4$^+$ CD45Rb transfer model (Mazmanian et al., *Nature* 453: 620-625 (2008)).

SUMMARY OF THE INVENTION

*B. fragilis* and polysaccharide A (PSA) of *B. fragilis* can be used to protect a subject from the development of colitis-associated colon cancer, for example by suppressing the expression of proinflammatory cytokines, chemokines and inducible nitric oxide synthase (iNOS). In some embodiments, methods of preventing and treating colorectal tumorigenesis are provided using a probiotic approach.

In one aspect, methods are provided for preventing, delaying the onset of or reducing the progression of colorectal tumorigenesis in a subject identified as at risk of colorectal tumorigenesis, comprising adjusting the composition of gut microbiota in the subject via administering to the subject a composition comprising *Bacteroides* bacteria.

In some embodiments, the *Bacteroides* is one or more of *B. fragilis, B. thetaiotaomicron, B. vulgatus*, or a mixture thereof. In some embodiments, the composition is a probiotic composition, a neutraceutical composition, a pharmaceutical composition, or a mixture thereof. In some embodiments, the composition comprises one or more zwitterionic polysaccharides (ZPS), Vitamin D, or a combination thereof. In some embodiments, the composition is administered via fecal transplantation. In some embodiments, the composition is administered via oral administration.

In some embodiments, the composition is administered intermittently, periodically, continuously, or chronically.

In some embodiments, the methods comprise measuring the expression level of a pro-inflammatory cytokine, a chemokine, and/or inducible nitric oxide synthase (iNOS) in the subject before and/or after the composition of gut microbiota is adjusted in the subject. In some embodiments, the pro-inflammatory cytokine is selected from the group consisting of TNFα, IL-6, IL-17A, and IL-23. In some embodiments, the chemokine is selected from the group consisting of monocyte chemoattractant protein 1 (MCP-1), macrophage inflammatory protein 2 (MIP-2), and chemokine ligand (KC).

In some embodiments, the methods comprise diagnosing a subject with a colorectal condition. In some embodiments, the colorectal condition is an intestinal inflammatory condition. In some embodiments, the intestinal inflammatory condition is selected from the group consisting of inflammatory bowel disease (IBD), Crohn's disease (CD), and ulcerative colitis (UC). In some embodiments, the intestinal inflammatory condition is UC.

In some embodiments, the methods comprise assessing the risk of colorectal tumorigenesis of a subject. In some embodiments, assessing the risk of colorectal tumorigenesis of the subject comprises looking for a family history of colorectal cancer of the subject, identifying a genetic mutation associated with colorectal cancer in the subject, testing for dysbiosis in the subject, or a combination thereof. In some embodiments, the dysbiosis comprises an over-representation of *Proteus mirabilis* and/or *Klebsiella Pneumonia*.

In some embodiments, the tumor-free time of the subject in which the composition of gut microbiota has been adjusted is increased in comparison to a reference tumor-free time in one or more subjects in which the composition of gut microbiota has not been adjusted. In some embodiments, the total size of one or more tumors in the subject in which the composition of gut microbiota has been adjusted is decreased in comparison to a reference total tumor size in one or more subjects in which the composition of gut microbiota has not been adjusted. In some embodiments, the total number of the tumors in the subject in which the composition of gut microbiota has been adjusted is decreased in comparison to a reference total tumor number in one or more subjects in which the composition of gut microbiota has not been adjusted. In some embodiments, the total size of one or more tumors in the subject in which the composition of gut microbiota has been adjusted is unchanged or changed at a slower pace in comparison to prior to treatment. In some embodiments, the total number of the tumors in the subject in which the composition of gut microbiota has been adjusted is unchanged or decreased in comparison to prior to treatment.

Further provided herein are methods for preventing, delaying the onset of or reducing the progression of colorectal tumorigenesis in a subject at risk of colorectal tumorigenesis, comprising administering to the subject a therapeutically effective amount of a pharmaceutical composition comprising zwitterionic polysaccharide (ZPS).

In some embodiments, the ZPS is derived from bacteria. In some embodiments, the ZPS is derived from intestinal bacteria. In some embodiments, the ZPS is derived from *Bacteroides* bacteria. In some embodiments, the *Bacteroides* bacteria is *B. fragilis, B. thetaiotaomicron*, or *B. vulgatus*. In some embodiments, the ZPS is polysaccharide A (PSA). In some embodiments, the pharmaceutical composition comprises *Bacteroides* bacteria, Vitamin D, or a combination thereof.

In some embodiments, the methods comprise diagnosing the subject with a colorectal condition. In some embodiments, the colorectal condition is an intestinal inflammatory condition. In some embodiments, the intestinal inflammatory condition is selected from the group consisting of inflammatory bowel disease (IBD), Crohn's disease (CD), and ulcerative colitis (UC). In some embodiments, the intestinal inflammatory condition is UC.

In some embodiments, the methods comprise assessing the risk of colorectal tumorigenesis of the subject. In some embodiments, assessing the risk of colorectal tumorigenesis of the subject comprises looking for a family history of colorectal cancer of the subject, identifying a genetic mutation associated with colorectal cancer in the subject, testing for dysbiosis in the subject, or a combination thereof. In some embodiments, the dysbiosis comprises an over-representation of *Proteus mirabilis* and/or *Klebsiella Pneumonia*.

In some embodiments, the pharmaceutical composition is administered orally to the subject.

In some embodiments, the methods comprise measuring the expression level of a pro-inflammatory cytokine, a chemokine, and/or inducible nitric oxide synthase (iNOS) in the subject after the pharmaceutical composition has been administered to the subject. In some embodiments, the pro-inflammatory cytokine is selected from the group consisting of TNFα, IL-6, IL-17A, and IL-23. In some embodiments, the chemokine is selected from the group consisting of monocyte chemoattractant protein 1 (MCP-1), macrophage inflammatory protein 2 (MIP-2), and chemokine ligand (KC).

In some embodiments, the tumor-free time of the subject to which the pharmaceutical composition has been administered is increased in comparison to a reference tumor-free time in subjects to which the pharmaceutical composition has not been administered. In some embodiments, the total size of one or more tumors in the subject to which the pharmaceutical composition has been administered is decreased in comparison to a reference total tumor size in one or more subjects to which the pharmaceutical composition has not been administered. In some embodiments, the total number of one or more tumors in the subject to which the pharmaceutical composition has been administered is decreased in comparison to a reference total tumor number in one or more subjects to which the pharmaceutical composition has not been administered. In some embodiments, the total size of one or more tumors in the subject to which the pharmaceutical composition has been administered is unchanged or changed at a slower pace in comparison to prior to treatment. In some embodiments, the total number of the tumors in the subject to which the pharmaceutical composition has been administered is unchanged or decreased in comparison to prior to treatment.

In another aspect, methods are provided for treating or ameliorating a colorectal cancer in a subject, comprising adjusting the composition of gut microbiota in the subject having the colorectal cancer.

In some embodiments, the methods comprise diagnosing the subject with a colorectal cancer. In some embodiments, the colorectal cancer is a colitis-associated colorectal cancer. In some embodiments, the colorectal cancer is a complication of inflammatory bowel disease (IBD).

In some embodiments, adjusting the composition of gut microbiota of the subject comprises administering to the subject a composition comprising *Bacteroides* bacteria. In some embodiments, the *Bacteroides* bacteria is *B. fragilis, B. thetaiotaomicron, B. vulgatus*, or a mixture thereof. In some embodiments, the composition is a probiotic composition, a neutraceutical composition, a pharmaceutical composition, or a mixture thereof. In some embodiments, the composition comprises ZPS, Vitamin D, or a combination thereof.

In some embodiments, the composition is administered via fecal transplantation. In some embodiments, the composition is administered via oral administration.

In a further aspect, methods are provided for relieving gastrointestinal (GI) distress of a subject having a colorectal condition, comprising: determining the colorectal condition of the subject; and relieving GI distress in the subject by adjusting the composition of gut microbiota in the subject.

In some embodiments, the colorectal condition is a colorectal cancer. In some embodiments, the colorectal cancer is a colitis-associated colorectal cancer. In some embodiments, the colorectal cancer is a complication of inflammatory bowel disease (IBD).

In some embodiments, the colorectal condition is an intestinal inflammatory condition. In some embodiments, the intestinal inflammatory condition is selected from the group consisting of IBD, Crohn's disease (CD), and ulcerative colitis (UC). In some embodiments, the intestinal inflammatory condition is IBD.

ΔPSA. (F) Comparison of KC level among control, mice colonized with *B. fragilis* and mice colonized with *B. fragilis* ΔPSA. (G) Comparison of iNOS level among control, mice colonized with *B. fragilis* and mice colonized with *B. fragilis* ΔPSA.

Figure 3:
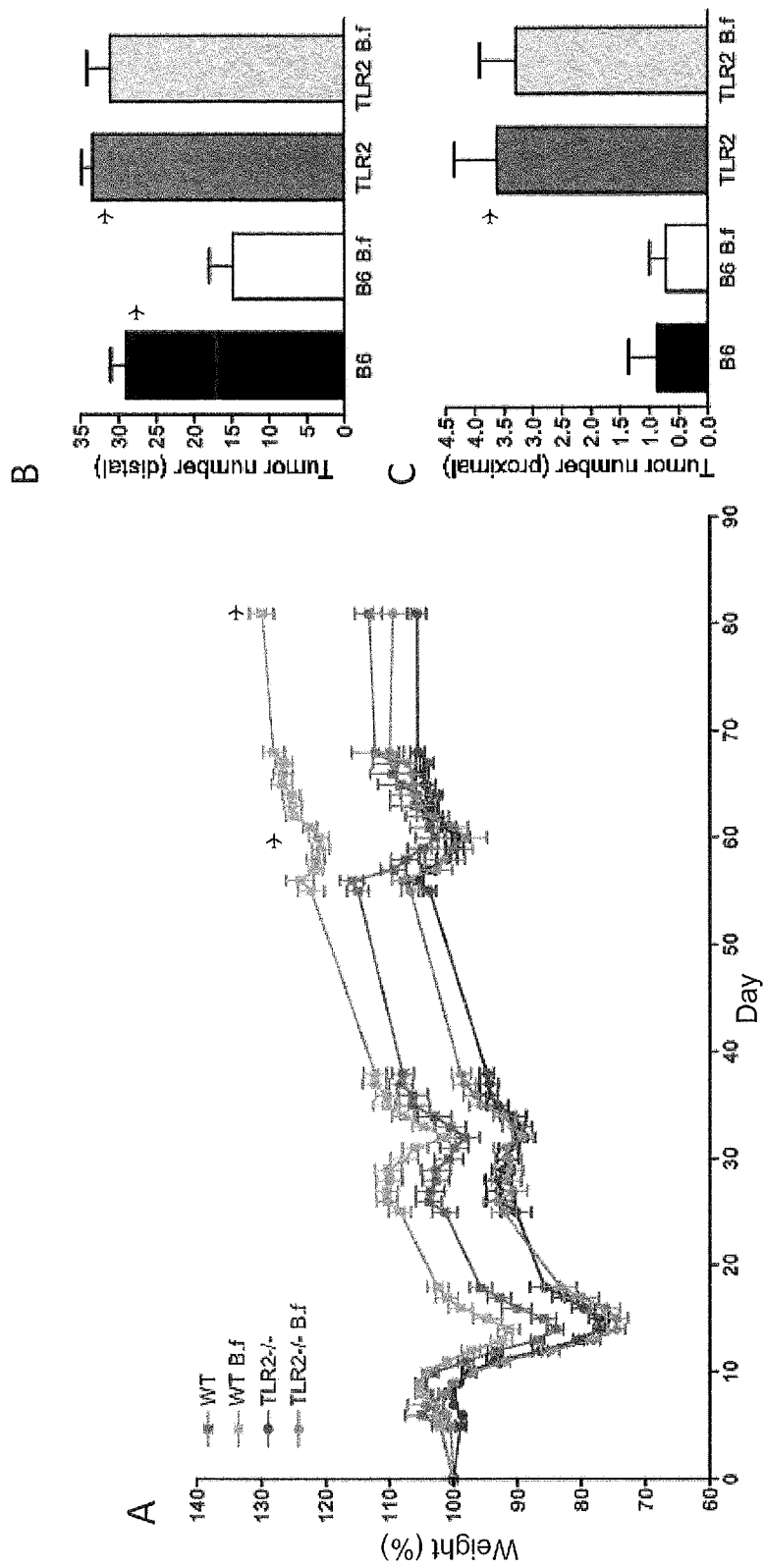

FIG. 3 shows TLR2 signaling is responsible for the protection by *B. fragilis* from the development of colon cancer in mice. (A) WT mice colonized with *B. fragilis* showed significantly decreased weight loss compared to WT mice treated PBS, whereas TLR2$^{-/-}$ mice showed similar degree of weight loss regardless of *B. fragilis* colonization. (B) The number of tumors in distal colon was significantly decreased in WT mice colonized with *B. fragilis* compared to WT mice treated with PBS, whereas TLR2$^{-/-}$ mice developed similar number of tumors in distal colon regardless of *B. fragilis* colonization. (C) More tumors were found in proximal colon of TLR2$^{-/-}$ mice with or without *B. fragilis* colonization in comparison to WT.

DETAILED DESCRIPTION OF THE PREFERRED EMBODIMENT

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

General Techniques

The practice of the present invention will employ, unless otherwise indicated, conventional techniques of molecular biology (including recombinant techniques), microbiology, cell biology, biochemistry, immunology, and pharmacology, which are within the skill of the art. Such techniques are explained fully in the literature, such as, *Molecular Cloning: A Laboratory Manual*, 2$^{nd}$ ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy*, 20$^{th}$ ed., (Lippincott, Williams & Wilkins 2003).

Definitions

Unless defined otherwise, all technical and scientific terms used herein have the same meaning as is commonly understood by one of ordinary skill in the art to which this invention belongs. See, e.g., *Dictionary of Microbiology and Molecular Biology* 2$^{nd}$ ed. (Singleton et al., J. Wiley & Sons 1994). All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

For the purposes of the present disclosure, the following terms are defined below.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

As used herein, the term "subject" is a vertebrate, such as a mammal. The term "mammal" is defined as an individual belonging to the class Mammalia and includes, without limitation, humans, domestic and farm animals, and zoo, sports, or pet animals, such as sheep, dogs, horses, cats or cows. In preferred embodiments, the subject is human.

As used herein, the term "treatment" refers to a clinical intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. In some embodiments, treatment may refer to a clinical intervention made to a cancer patient, particularly a patient suffering from colorectal cancer. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may prevent, delay the onset of or reduce the progression of colorectal tumorigenesis of the subject, including subjects having an intestinal inflammatory condition such as IBD. As used herein, the term "prevention" refers to any activity that avoids, delays the onset of or reduces the progression of colorectal cancer. This takes place at primary, secondary and tertiary prevention levels, wherein: a) primary prevention avoids the development of colorectal cancer; b) secondary prevention activities are aimed at early stages of the colorectal cancer treatment, thereby increasing opportunities for interventions to prevent progression of the colorectal cancer and emergence of symptoms; and c) tertiary prevention reduces the negative impact of an already established colorectal cancer by, for example, restoring function and/or reducing any colorectal cancer or related complications.

As used herein, the term "neutraceutical" refers to a food stuff (as a fortified food or a dietary supplement) that provides health benefits.

As used herein, the term "probiotic" refers to live microorganisms, which, when administered in adequate amounts, may confer a health benefit on the host. The probiotics may be available in foods and dietary supplements (for example, but not limited to capsules, tablets, and powders). Non-limiting examples of foods containing probiotics include dairy products such as yogurt, fermented and unfermented milk, smoothies, butter, cream, hummus, kombucha, salad dressing, miso, tempeh, nutrition bars, and some juices and soy beverages. In some embodiments, the probiotics may be present naturally.

The term "zwitterionic polysaccharide (ZPS)" as used herein indicates synthetic or natural polymers comprising one or more monosaccharides joined together by glicosidic bonds, and including at least one positively charged moiety and at least one negatively charged moiety. Zwitterionic polysaccharides include but are not limited to polymers of any length, from a mono- or di-saccharide polymer to polymers including hundreds or thousands of monosaccharides. In some embodiments, a zwitterionic polysaccharide can include repeating units wherein each repeating unit includes from two to ten monosaccharides, a positively charged moiety (e.g., an free positively charged amino moiety) and a negatively charged moiety (such as sulfonate, sulfate, phosphate and phosphonate). In some embodiments, the ZPS can have a molecular weight from about 500 Da to about 2,000,000 Da. In some embodiments, the ZPS can have a molecular weight from about 200 to about 2500. ZPSs can be isolated from natural sources, and in particular from bacterial sources, e.g., by purification. Exemplary ZPSs include but are not limited to PSA and PSB from *B. fragilis*, CP5/CD8 from *Staphylococcus aureus*, and Sp1/CP1 from *Streptococcus pneumonia*. ZPSs can also be produced by chemical or biochemical methods, as well as by recombinant microorganism technologies all identifiable by a skilled person. Thus, those methods and technologies will not be further described herein in detail.

The term "polysaccharide A" (or PSA, or PSA ligand) as used herein indicates a molecule produced by the PSA locus of *B. fragilis* and derivatives thereof which include but are not limited to polymers of the repeating unit {→3) α-d-AAT Galp(1→4)-[β-d-Galf(1→3)] α-d-GalpNAc(1→3)-[4,6-pyruvate]-β-d-Galp(1→}, where AATGal is acetamido-amino-2,4,6-trideoxygalactose, and the galactopyranosyl residue is modified by a pyruvate substituent spanning O-4 and O-6. The term "derivative" as used herein with reference to a first polysaccharide (e.g., PSA), indicates a second polysaccharide that is structurally related to the first polysaccharide and is derivable from the first polysaccharide by a modification that introduces a feature that is not present in the first polysaccharide while retaining chemical properties, biological properties, or both, of the first polysaccharide. Accordingly, a derivative polysaccharide of PSA, usually differs from the original polysaccharide by modification of the repeating units or of the saccharidic component of one or more of the repeating units that might or might not be associated with an additional function not present in the original polysaccharide. A derivative polysaccharide of PSA retains however one or more functional activities that are herein described in connection with the anti-inflammatory activity of PSA.

The term "Vitamin D" as used herein includes any one or a combination of a group of fat-soluble prohormones (D1-D5: 25 D, 1,25 D see below), which encourages the absorption and metabolism of calcium and phosphorous. Five forms of vitamin D have been discovered, vitamin $D_1$, $D_2$, $D_3$, $D_4$, $D_5$. The two forms that seem to matter to humans the most are vitamins $D_2$ (ergocalciferol) and $D_3$ (cholecalciferol). Vitamin D for humans is obtained from sun exposure, food and supplements. It is biologically inert and has to undergo two hydroxylation reactions to become active in the body. The term may also include 1,25-dihydroxycholecalciferol or 1,25-dihydroxyvitamin ("1,25-D"), which is considered the active form of vitamin D. 1,25 D is derived from its precursor 25-hydroxyvitamin-D(D-25) by the enzyme 1α-hydroxylase ("CYP27B1") encoded by the CYP27B1 gene, (NG_007076.1 *Homo Sapiens*) CYP27B1.

As used herein, the term "cytokine" refers to a secreted protein or active fragment or mutant thereof that modulates the activity of cells of the immune system. Examples of cytokines include, without limitation, interleukins, interferons, chemokines, tumor necrosis factors, colony-stimulating factors for immune cell precursors, and the like.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

Prevention of Colorectal Tumorigenesis

We observed that mice colonized with *B. fragilis* developed significantly less colorectal tumors than mice with *B. fragilis* ΔPSA or control mice using an azoxymethane (AOM)/dextran sulfate sodium (DSS)-induced colon cancer model. The finding is especially remarkable because *B. fragilis* did not protect against DSS-induced colitis in a mouse model (data not shown). Proinflammatory cytokines and signature genes of colon homogenates were down-regulated by *B. fragilis* colonization during the development of colon cancer. Without being held to any particular theory, it is believed that toll-like receptor (TLR) 2 signaling is responsible to protect *B. fragilis* colonized mice from tumor development.

Therefore, in one aspect, the present invention provides methods for preventing, delaying the onset of or reducing the progression of colorectal tumorigenesis in a subject. In some embodiments, the methods comprise adjusting the composition of gut microbiota in the subject. In some embodiments, the subject is a human.

In some embodiments, the colorectal tumorigenesis may be associated with an intestinal inflammatory condition. In some embodiments, the colorectal tumorigenesis may be associated with colitis or IBD. Chronic inflammation is a known risk factor for tumorigenesis, and epidemiological data suggest that up to 15% of human cancer incidence is associated with inflammation (Mantovani et al., *Nature* 454: 436-444 (2008)); Kuper et al., *J. Intern. Med.* 248: 171-183 (2000)). Inflammation-induced colorectal cancer develops in patients with chronic IBD (Jawad et al, *Recent Results Cancer Rec.* 185: 99-115 (2011)), which has been shown to be regulated by caspase-1 and NLRC4 (Hu et al., *Proc. Natl. Acad. Sci.* 107: 21635-21640 (2010)). Chronic formation of reactive oxygen species and chronic epithelial exposure or inflammatory stimuli, such as IL-6 and TNF-α have been implicated in the tumorigenesis (Coussens & Werb, *Nature* 420: 860-867 (2002); Popivanova et al., *J. Clin. Invest.* 118: 560-570 (2008); Becker et al., *Immunity* 21: 491-501 (2004);

Bollrath et al., *Cancer Cell* 15: 91-102 (2009); Grivennikov et al., *Cancer Cell* 15: 103-113 (2009)). A number of intestinal inflammatory conditions are known to one of ordinary skill in the art, including but not limited to, colitis, IBD, Chron's disease, ulcerative colitis and pancolitis. Severity of the inflammation and the longer time of the inflammation have been linked to an increased risk of colorectal cancer tumorigenesis (Xie & Itzkowitz, *World J. Gastroenterol.* 14: 378-89 (2008); Triantafillidis et al., *Anticancer Res.* 29: 2727-37 (2009)).

For the presently disclosed preventative methods, it may be desirable to select subjects that are at an increased risk of colorectal tumorigenesis. In some embodiments, known risk factors that increase the likelihood of colorectal tumorigenesis may be used to evaluate the suitability of a subject for the preventative methods disclosed herein. These risk factors include, but are not limited to, duration of colitis, extent of colitis, a family history of colorectal cancer, and, according to some studies, early disease onset and more severely active inflammation, greater extent of colonic involvement, primary sclerosing cholangitis, young age of IBD onset, backwash ileitis, history of dysplasia, etc. Raised dysplastic lesions, also known as dysplasia associated lesion or mass (DALM), or flat dysplastic lesions may significantly increase the likelihood of a subject to develop colitis-associated colorectal cancer. Additionally, a number of genetic syndromes have been known to be associated with higher rates of colorectal cancer, such as hereditary non-polyposis colorectal cancer (HNPCC or Lynch syndrome), Gardner syndrome and familial adenomatous polyposis (FAP).

Severity of inflammation or diagnosis/staging of dysplasia or cancer in subjects may be assessed using a number of techniques, including but not limited to, histology, endoscopy, colonoscopy, chromoendoscopy, biopsy, etc. For the assessment of inflammation or diagnosis/staging of dysplasia or cancer, multiple biopsy specimens may be required. In some embodiments, at least 1, 2, 3, 4, 5, 10, 15, 20, 25, 30 or more biopsy specimens are taken from the subject.

Another risk factor that may increase a subject's susceptibility to colorectal tumorigenesis is the composition of gut microbiota. Shifts in the intestinal microenvironment may lead to changes in the microbiota known as dysbiosis, which in turn may increase susceptibility to intestinal inflammation and colorectal tumorigenesis (Mazmanian et al., *Nature* 453: 620-625 (2008); Garrett et al., *Cancer Cell* 16: 208-19 (2009)). *Proteus mirabilis* and/or *Klebsiella Pneumonia* were found to be over-represented in mice that spontaneously develop dysbiosis and colitis (Garrett et al., *Cell Host Microbe* 8: 292-300 (2010)). Other dysbiosis conditions that may contribute to colorectal cancer tumorigenesis include, but are not limited to, increased colonization of segmented filamentous bacteria (SFB), *Helicobacter hepaticus, Helicobacter pylori*, Actinobacteria or Ptoteobacteria, and/or decreased colonization of Firmicutes or *Bacteroides* bacteria. Dysbiosis conditions that may contribute to colorectal tumorigenesis may also include a genetic mutation in commensal bacteria. For example, deletion of the commensal colonization factor (ccf) gene in *B. fragilis* has been shown to result in colonization defects in mice (Lee et al., *Nature* 501: 426-29 (2013)).

In some embodiments, a combination of risk factors, such as genetic risk factors, intestinal inflammatory conditions, and/or gut microbiota, may be combined to evaluate a subject's susceptibility to colorectal tumorigenesis. A subject identified as at an increased risk of colorectal tumorigenesis may be treated with the preventative methods disclosed herein. In some embodiments, a subject with an intestinal inflammatory condition, such as IBD, may be treated with the preventative methods disclosed herein. In some embodiments, a subject with ulcerative colitis may be treated with the preventative methods disclosed herein. In some embodiments, a subject with chronic IBD, i.e., which has had IBD for 7, 8, 9, 10, 20, 30, 40 or more years, may be treated with the preventative methods disclosed herein.

In some embodiments, known molecular biomarkers of colorectal tumorigenesis may be used to identify a subject that is at an increased risk of colorectal tumorigenesis to be treated with the preventative methods disclosed herein. A number of biomarkers are well known in the art that may contribute to colorectal tumorigenesis, including but not limited to, APC, β-catenin, TP53, TGF-β, DCC (Deleted in Colorectal Cancer), SMAD, AXIN1, AXIN2, TCF7L2, or NKD1, KRAS, RAF, and PI3K, PTEN, CTNNB1, FAM123B, SOX9, ATM, and ARID1A, ACVR2A, TGFBR2, MSH3, MSH6, SLC9A9, TCF7L2, and BRAF, MYC, etc. TP53 mutation, Cox-2, aneuploidy, methylation of the hMLH1, p16INK4a, and E-cadherin promoter, microsatellite instability (MSI), sialyl-Tn, TP53 loss of heterogeneity (LOH), DCC, c9src, k-ras, and APC have been showed to occur in colitis-associated colorectal cancer (Itzkowitz & Harpaz, *Gastroenterology* 126: 1634-1648 (2004)). In some embodiments, the molecular biomarkers may be used to monitor the progression (or lack thereof) of colorectal cancer in a subject under treatment.

As used herein, "preventing, delaying or reducing colorectal tumorigenesis" may include, but not limited to, delaying the onset of dysplasia or colorectal cancer, slowing the progression of colorectal cancer from an early stage to a more advanced stage, delaying or preventing the transformation of a benign tumor to a malignant tumor, delay or preventing the metastasis of the tumor, etc. Colorectal tumorigenesis may also refer to recurrence of colorectal cancer after remission induced by surgery, chemotherapy, radiation therapy, etc. In some embodiments, the presently disclosed methods may be used to prevent or delay the development of precancers, such as tubular adenoma, colorectal villous adenoma, or colonic polyp. In some embodiments, the subject treated with the methods disclosed herein is tested for the development of tubular adenoma, colorectal villous adenoma, or colonic polyp. Onset of colorectal cancer may refer to tumor budding. In some embodiments, the subject treated with the methods disclosed herein is tested for tumor budding. Staging of colorectal cancer may be made according to the TNM staging system from the WHO organization, the UICC and the AJCC. Biopsy specimens are graded pathologically as negative, indefinite for dysplasia, low-grade dysplasia, high-grade dysplasia, or invasive cancer. In some embodiments, the subject treated with the methods disclosed herein is graded pathologically for stage of colorectal cancer.

One of ordinary skill in the art should be able to appreciate that a variety of parameters may be used to characterize the preventative effect of the methods disclosed herein. For example, the preventative effect may be characterized as the tumor-free period for the treated subject, the total number of tumors in the treated subject, the total weight of tumors in the treated subject, or a combination thereof. In some embodiments, the subject treated with the methods disclosed herein is assessed for the tumor-free period, the total number of tumors, the total weight of tumors in the treated subject, or a combination thereof. In some embodiments, the tumors may be tumors of distal colon, proximal colon, or both. To characterize the preventative effect, a reference value may be established based on one or more control subjects that are not treated with the methods disclosed herein. In some embodiments, the treated subject may show an increase of about 5%, about 10%, about 15%, about 20%, about 25%, about 30%, about 35%, about 40%, about 45%, about 50%, about 60%, about 70%, about 80%, about 90%, about 100%, about 200%, about 300%, about 400%, about 500% or more in the tumor-free period in comparison to the reference value. In some embodiments, the treated subject may show a decrease of about 5%, about 10%, about 15%, about 20%, about 25%, about 30%, about 35%, about 40%, about 45%, about 50%, about 60%, about 70%, about 80%, about 90%, about 95%, about 99% or about 100%, or a range between any two of these values in the total number of tumors in comparison to the reference value. In some embodiments, the treated subject may show a decrease of about 5%, about 10%, about 15%, about 20%, about 25%, about 30%, about 35%, about 40%, about 45%, about 50%, about 60%, about 70%, about 80%, about 90%, about 95%, about 99% or about 100%, or a range between any two of these values in the total weight of tumors in comparison to prior to treatment. In some embodiments, the treated subject may show a decrease of about 5%, about 10%, about 15%, about 20%, about 25%, about 30%, about 35%, about 40%, about 45%, about 50%, about 60%, about 70%, about 80%, about 90%, about 95%, about 99% or about 100%, or a range between any two of these values in the total number of tumors in comparison to prior to the treatment. In some embodiments, the treated subject may show a decrease of about 5%, about 10%, about 15%, about 20%, about 25%, about 30%, about 35%, about 40%, about 45%, about 50%, about 60%, about 70%, about 80%, about 90%, about 95%, about 99% or about 100%, or a range between any two of these values in the total weight of tumors in comparison to prior to the treatment.

Other than colorectal cancer, other types of cancer or cancer-like diseases such as small intestinal adenocarcinoma, Squamous cell carcinoma of the anus, cholangiocarcinoma, hepatobiliary cancers, and hematologic malignancies such as leukemia, hematopoietic cancer, lymphoma, myeloid leukemia may also be prevented, delayed, reduced or treated by the methods disclosed herein.

Adjustment of Gut Microbiota

Humans are colonized with a great abundance and diversity of microbes, which play a critical role in regulating health and disease. Dysbiosis of the commensal microbiota is implicated in the pathogenesis of several human ailments, including IBD, obesity and cardiovascular disease (Blumberg and Powrie, *Sci. Transl. Med.* 4: 137rv7 (2012); Clemente et al., *Scand. J. Gastroenterol.* 47: 943-50 (2012)).

In some embodiments, colorectal tumorigenesis may be prevented, delayed, or reduced through the adjustment of the composition of gut microbiota in a subject susceptible to developing colorectal cancer. Adjustment of composition of gut microbiota refers to changing the composition of the bacteria in the gut. Adjustment of the composition of gut microbiota in the subject can be achieved by, for example, fecal transplantation (also known as fecal microbiota transplantation (FMT), fecal bacteriotherapy or stool transplant). Fecal transplantation can include a process of transplantation of fecal bacteria from a healthy donor, for example a subject without IBD, to a recipient (e.g., a subject suffering from IBD). The procedure of fecal transplantation can include single or multiple infusions (e.g., by enema) of bacterial fecal flora from the donor to the recipient. In some embodiments, methods disclosed herein consist essentially of adjusting the composition of gut microbiota in a subject susceptible to colorectal cancer. In some embodiments, methods disclosed herein consist of adjusting the composition of gut microbiota in a subject susceptible to colorectal cancer. In some embodiments, methods disclosed herein are not combined with other pharmaceutical(s), e.g., antibiotics, anti-inflammatory drug(s) or chemotherapeutics, e.g., 5-Fluorouracil, Capecitabine, oxaliplatin, Irinotecan, etc.

In some embodiments, adjusting the composition of gut microbiota in the subject includes administering the subject a composition comprising bacteria, for example, a composition comprising *Bacteroides* bacteria. In some embodiments, the *Bacteroides* bacteria comprise *B. fragilis*, *B. thetaiotaomicron*, *B. vulgatus*, or a mixture thereof. In some embodiments, the composition may comprise *B. fragilis* and *B. thetaiotaomicron*. In some embodiments, the composition may comprise *B. fragilis* and *B. vulgatus*. In some embodiments, the composition may comprise *B. thetaiotaomicron* and *B. vulgatus*. In some embodiments, the *Bacteroides* bacteria can be *B. fragilis*. The composition comprising bacteria, for example a composition comprising *Bacteroides* bacteria, can be administered to the subject via various routes. For example, the composition can be administered to the subject via oral administration, rectal administration, transdermal administration, intranasal administration or inhalation. In some embodiments, the composition is administered to the subject orally. The composition comprising bacteria, such as *Bacteroides* bacteria, can also be in various forms. For example, the composition can be a probiotic composition, a neutraceutical, a pharmaceutical composition, or a mixture thereof.

In some embodiments, the composition is a probiotic composition. Each dosage for human and animal subjects preferably contains a predetermined quantity of the bacteria calculated in an amount sufficient to produce the desired effect. The actual dosage forms will depend on the particular bacteria employed and the effect to be achieved. The composition comprising bacteria, for example, a composition comprising *Bacteroides* bacteria, can be administered alone or in combination with one or more additional probiotic, neutraceutical, or therapeutic agents. Administration "in combination with" one or more further additional probiotic, neutraceutical, or therapeutic agents includes both simultaneous (at the same time) and consecutive administration in any order. Administration can be chronic or intermittent, as deemed appropriate by the supervising practitioner, particularly in view of any change in the disease state or any undesirable side effects. "Chronic" administration refers to administration of the composition in a continuous manner while "intermittent" administration refers to treatment that is done with interruption.

The composition of gut microbiota of the treated subject may be monitored before, during, or after the treatment period. A variety of monitoring techniques are known to one of ordinary skill in the art. For example, sequencing, PCR or microarray analysis may be used to identify the species and amount of bacteria present in the gut microbiota. ELISA assays using antibodies that specifically bind to bacterial antigens may also be used to identify and quantify the bacteria species in the gut microbiota. In some embodiments, administrating the composition comprising bacteria, for example, a composition comprising *Bacteroides* bacteria, may also be adjusted according to the results from monitoring the composition of gut microbiota. For example, if the administered bacteria composition fully restores the normal colonization state of the bacteria, further administration of the composition may be suspended in view of further monitoring results.

In some embodiments, administrating the composition comprising bacteria, for example, a composition comprising *Bacteroides* bacteria, may also be adjusted according to the subject's intestinal inflammatory condition. Administration of the bacteria composition may be suspended if the intestinal inflammatory condition, such as IBD, Crohn's disease, ulcerative colitis, etc., has been cured permanently or has gone into remission. The subject's intestinal inflammatory condition may be assessed using a number of techniques, including but not limited to, histology, endoscopy, colonoscopy, chromoendoscopy, biopsy, etc. In some embodiments, multiple biopsy specimens may be required. In some embodiments, at least 1, 2, 3, 4, 5, 10, 15, 20, 25, 30 or more biopsy specimens are taken from the subject.

In the methods disclosed herein, the amount of bacteria, for example *Bacteroides* bacteria (e.g., *B. fragilis*), administered to the subject in need of treatment can be determined according to various parameters such as the age, body weight, response of the subject, condition of the subject to be treated; the type and severity of intestinal inflammatory condition, IBD, or the pathological conditions with one or more symptoms of IBD; the form of the composition in which the bacteria is included; the route of administration; and the required regimen. The severity of the condition may, for example, be evaluated, in part, by standard prognostic evaluation methods. For example, the amount of bacteria can be titrated to determine the effective amount for administering to the subject in need of treatment. One of ordinary skill in the art would appreciate that the attending physician would know how to and when to terminate, interrupt or adjust administration of bacteria due to toxicity or organ dysfunctions. Conversely, the attending physician would also know to adjust treatment to higher levels if the clinical response were not adequate (precluding toxicity).

For example, the bacteria may be administered at a dose of at least $10^3$ CFU, optionally at least $10^4$ CFU, optionally at least $10^5$ CFU, optionally at least $10^6$ CFU, optionally at least $10^7$ CFU, optionally at least $10^8$ CFU, or optionally at least $10^9$ CFU. In some embodiments, the bacteria may be administered at a dose of $10^3$ to $10^{12}$ CFU, optionally at a dose of $10^4$ to $10^{11}$ CFU, optionally at a dose of $10^5$ to $10^{10}$ CFU, optionally at a dose of $10^6$ to $10^{10}$ CFU, or optionally at a dose of $10^7$ to $10^{10}$ CFU. In some embodiments, the bacteria may be administered at optionally at a dose of $10^7$ to $10^{10}$ CFU. In some embodiments, the bacteria may be administered at optionally at a dose of $5 \times 10^9$ to $7 \times 10^{10}$ CFU.

In some embodiments, the subject being treated may be a human. In some embodiments, the subject being treated may be a non-human mammal. A program comparable to that discussed above may be used in veterinary medicine.

Methods for assessing the susceptibility of a subject to probiotic treatment are provided herein. The methods can include: determining the level of a *B. fragilis*-responsive metabolite in the subject; and comparing the level of the *B. fragilis*-responsive metabolite in the subject to a reference level of the metabolite in subjects suffering from an intestinal inflammatory condition, wherein substantial identity between the blood level of the metabolites in the subject and the reference level indicates that the subject is susceptible to the probiotic treatment, for example *B. fragilis* probiotic treatment. In some embodiments, the methods include determining the level of two or more *B. fragilis*-responsive metabolites in the subject; and comparing the level of each of the two or more *B. fragilis*-responsive metabolites in the subject to the reference level of each of the two or more *B. fragilis*-responsive metabolites, wherein substantial identity between the blood levels of the metabolites in the subject and the reference levels indicates an increased susceptibility of the subject to the probiotic treatment.

The level of the metabolite can be the level of the metabolite in circulation of the subject. For example, the level of the metabolite is the level of the metabolite in blood or other body fluids (e.g., cerebrospinal fluid, pleural fluid, amniotic fluid, semen, or saliva) of the subject. In some embodiments, the level of the metabolite is the blood level of the metabolite in the subject. The blood level of the metabolite can be, for example, serum level or plasma level of the metabolite. In some embodiments, the level of the metabolite is the urine level of the metabolite in the subject.

*B. fragilis*-Responsive Metabolites

As used herein, the term "*B. fragilis*-responsive metabolite" refers to a metabolite whose level has been determined to be altered by *B. fragilis* treatment. For example, the level of the metabolite may be altered in circulation of the subject after *B. fragilis* treatment. In some embodiments, the level of the metabolite is altered in blood, serum, plasma, body fluids (e.g., cerebrospinal fluid, pleural fluid, amniotic fluid, semen, or saliva), urine, and/or feces of the subject after *B. fragilis* treatment. The *B. fragilis*-responsive metabolite can be increased or decreased in level after *B. fragilis* treatment.

As disclosed herein, *B. fragilis*-responsive metabolite can be determined by comparing the pre-treatment level of a metabolite in a subject, for example a subject suffering from an intestinal inflammatory condition, with the level of a metabolite in the subject after *B. fragilis* treatment. One of ordinary skill in the art will appreciate that variability in the level of metabolites may exist between individuals, and a reference level for a *B. fragilis*-responsive metabolite can be established as a value representative of the level of the metabolites in a population of subjects suffering from an intestinal inflammatory condition for the comparison.

Non-limiting examples of *B. fragilis*-responsive metabolites are provided in Table 1.

TABLE 1

| Exemplary *B. fragilis*-responsive metabolites | |
|---|---|
| sarcosine (N-Methylglycine) | inosine |
| aspartate | adenosine |
| 3-ureidopropionate | adenosine 5'-monophosphate (AMP) |
| glutarate (pentanedioate) | guanosine 5'-monophosphate (5'-GMP) |
| tyrosine | urate |
| 3-(4-hydroxyphenyl)lactate | 2'-deoxycytidine |
| 3-phenylpropionate (hydrocinnamate) | uracil |

TABLE 1-continued

Exemplary *B. fragilis*-responsive metabolites

| | |
|---|---|
| serotonin (5HT) | pseudouridine |
| 3-methyl-2-oxobutyrate | nicotinamide |
| 3-methyl-2-oxovalerate | catechol sulfate |
| 4-methyl-2-oxopentanoate | salicylate |
| isobutyrylcarnitine | equol sulfate |
| 2-methylbutyroylcarnitine | erythritol |
| isovalerylcarnitine | dodecanedioate |
| 2-hydroxybutyrate (AHB) | tetradecanedioate |
| arginine | hexadecanedioate |
| ornithine | octadecanedioate |
| 2-aminobutyrate | undecanedioate |
| 4-guanidinobutanoate | 12-HETE |
| 5-oxoproline | propionylcarnitine |
| glycylvaline | butyrylcarnitine |
| gamma-glutamyltryptophan | valerylcarnitine |
| TDTEDKGEFLSEGGGV | 3-dehydrocarnitine |
| TDTEDKGEFLSEGGGVR | hexanoylcarnitine |
| sorbitol | octanoylcarnitine |
| pyruvate | choline |
| ribitol | chiro-inositol |
| ribose | pinitol |
| ribulose | 3-hydroxybutyrate (BHBA) |
| xylitol | 1,2-propanediol |
| citrate | 1-linoleoylglycerophosphoethanolamine |
| fumarate | 1-arachidonoylglycerophosphoethanolamine |
| malate | 2-arachidonoylglycerophosphoethanolamine |
| linoleate (18:2n6) | 1-stearoylglycerophosphoinositol |
| linolenate [alpha or gamma; (18:3n3 or 6)] | 1-linoleoylglycerophosphoinositol |
| dihomo-linolenate (20:3n3 or n6) | 1-arachidonoylglycerophosphoinositol |
| docosapentaenoate (n3 DPA; 22:5n3) | 1-palmitoylplasmenylethanolamine |
| docosapentaenoate (n6 DPA; 22:5n6) | hypoxanthine |
| docosahexaenoate (DHA; 22:6n3) | eicosenoate (20:1n9 or 11) |
| heptanoate (7:0) | dihomo-linoleate (20:2n6) |
| pelargonate (9:0) | mead acid (20:3n9) |
| laurate (12:0) | adrenate (22:4n6) |
| myristate (14:0) | 8-hydroxyoctanoate |
| palmitate (16:0) | 3-hydroxydecanoate |
| palmitoleate (16:1n7) | 16-hydroxypalmitate |
| margarate (17:0) | 13-HODE + 9-HODE |

TABLE 1-continued

Exemplary *B. fragilis*-responsive metabolites

| | |
|---|---|
| stearate (18:0) | 12,13-hydroxyoctadec-9(Z)-enoate |
| oleate (18:1n9) | 9,10-hydroxyoctadec-12(Z)-enoic acid |
| stearidonate (18:4n3) | adipate |
| suberate (octanedioate) | 2-hydroxyglutarate |
| sebacate (decanedioate) | pimelate (heptanedioate) |
| azelate (nonanedioate) | |

The methods of adjusting the composition of gut microbiota disclosed herein may be combined with other medications and/or dietary supplements that have anti-inflammatory effects, such as aspirin or other NSAID, 5-aminosalicylates (5-ASA), systemic steroids, topical steroids, 6-mercaptopurine or azathioprine. Folate supplement, ursodiol and other anti-oxidants, statins may also be used in combination with the methods of adjusting the composition of gut microbiota disclosed herein. In some embodiments, the methods of adjusting the composition of gut microbiota disclosed herein may be combined with Vitamin D. Vitamin D has been known to enhance the protective effect of *B. fragilis* and PSA against IBD (U.S. Patent Publication No. 2013/0064859, the content of which is herein expressly incorporated by reference in its entirety).

Zwitterionic Polysaccharide

PSA was shown to contribute to the anti-colitis activity of *B. fragilis* colonization in an experimental mouse model, as well as to the prevention of colorectal cancer tumorignensis by *B. fragilis* colonization in a mouse model of colitis-induced colorectal cancer. Purified PSA was also shown to suppress pro-inflammatory IL-17 production, and prevent intestinal inflammation through induction of IL-10 expression.

Therefore, further provided herein are methods of preventing, delaying or reducing colorectal tumorigenesis in a subject, comprising administering to the subject a therapeutically effective amount of a pharmaceutical composition comprising a zwitterionic polysaccharide (ZPS) to prevent colorectal tumorigenesis, delay the onset of colorectal tumorigenesis, or reduce the progression of colorectal tumorigenesis. In some embodiments, the pharmaceutical composition may comprise more than one ZPSs.

Bacterial ZPSs isolated from strains of *B. fragilis, S. aureus*, and *S. pneumoniae* type 1 represent an unusual group of bacterial carbohydrates. ZPSs which include both positively and negatively charged groups have unique immunological properties: molecules as small as 17 kDa elicit a potent $CD4^+$ T cell response in vitro, and ZPS-activated T cells confer protection against experimental intraabdominal abscess formation (Kalka-Moll et al., *J. Immunol.* 164: 719-24 (2000); U.S. Patent Publication No. 2013/0039949, the content of which is herein expressly incorporated by reference in its entirety). *B. fragilis* polysaccharide A (PSA) as used herein refers to *B. fragilis* capsular polysaccharide A as disclosed, for example, in U.S. Pat. No. 5,679,654, the content of which is herein expressly incorporated by reference in its entirety. This polysaccharide has a tetrasaccharide repeating unit containing one cationic free amine and one anionic carboxylate in each repeating unit. (Tzianabos et al., *J. Biol. Chem.* 267: 18230-5 (1992); U.S. Pat. Nos. 5,679,654 and 5,700,787). PSA is also known as PSA1.

ZPS as used herein in some embodiments refers to a naturally occurring polysaccharide having certain structural features including the presence of repeating units, each with at least one positively charged moiety and at least one negatively charged moiety. A ZPS as used herein in one embodiment refers to polysaccharides that have been modified to include the structural features including the presence of repeating units, each with at least one positively charged moiety and at least one negatively charged moiety.

In some embodiments ZPSs have a plurality of repeating units, wherein each repeating unit comprises two to ten monosaccharides and a positively charged free amino moiety and a negatively charged moiety selected from the group consisting of carboxylate, phosphate, phosphonate, sulfate, and sulfonate. Molecular weights of the ZPSs useful in the invention typically have molecular weights between 500 Da and 2,000,000 Da, although smaller and larger polysaccharides can also be used. For example, the polysaccharide can be as small as one or two saccharide units. In some embodiments a disaccharide including only one non-acetylated amino sugar and one uronic acid is sufficient to stimulate T-cell proliferation.

Polysaccharides that can be used in some embodiments include those naturally occurring polysaccharides that include the requisite charged groups. See, e.g., U.S. Pat. No. 8,206,726, the content of which is herein expressly incorporated by reference in its entirety. In addition to the naturally occurring polysaccharides, polysaccharide repeating units that consist of at least one N-acetyl sugar and at least one uronic acid (sugar with a negatively charged carboxyl group) can be modified to produce the immune response of the present invention. Molecules which may be de-N-acetylated include *Salmonella typhi* capsular polysaccharide (VI antigen), *E. coli* K5 capsular polysaccharide, *S. aureus* type 5 capsular polysaccharide, Group B *Streptococcus* type III capsular polysaccharide, and *Rhizobium meliloti* exopolysaccharide II. These polysaccharides and their modification have been described in U.S. Pat. No. 5,679,654, the content of which is incorporated herein in its entirety.

In some embodiments, the pharmaceutical composition comprising ZPS disclosed herein may be combined with Vitamin D.

The ZPS may be administered subcutaneously, transdermally, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The ZPS may also be administered in slow release dosage forms.

In the methods disclosed herein, the amount of ZPS, for example PSA, administered to the subject as risk for colorectal tumorigenesis can be determined according to various parameters such as the age, body weight, response of the subject, condition of the subject to be treated; the type and severity of intestinal inflammatory condition, IBD, or the pathological conditions with one or more symptoms of IBD; the form of the composition in which ZPS is included; the route of administration; and the required regimen. The severity of the condition may, for example, be evaluated, in part, by standard prognostic evaluation methods. For example, the amount of ZPS can be titrated to determine the effective amount for administering to the subject in need of treatment. One of ordinary skill in the art would appreciate that the attending physician would know how to and when to terminate, interrupt or adjust administration of bacteria due to toxicity or organ dysfunctions. Conversely, the attending physician would also know to adjust treatment to higher levels if the clinical response were not adequate (precluding toxicity).

For example, the ZPS may be administered at a dose of at least 0.01 µg, optionally at least 0.1 µg, optionally at least 1 µg, optionally at least 0.5 µg, optionally at least 1 µg, optionally at least 5 µg, optionally at least 10 µg, optionally at least 50 µg, optionally at least 100 µg, optionally at least 500 µg, or optionally at least 1 mg. In some embodiments, the ZPS may be administered at a dose of 1 µg to 1000 mg, optionally at a dose of 0.005-500 mg, optionally at a dose of 0.01-200 mg, optionally at a dose of 0.05-100 mg, optionally at a dose of 0.1-50 mg, optionally at a dose of 1-20 mg, optionally at a dose of 0.1-5 mg, or optionally at a dose of about 1-5 mg. In some embodiments, the ZPS is administered at a dose of 1 µg to 10 mg. In some embodiments, the ZPS is administered at a dose of 25 µg to 1 mg.

In some embodiments, the subject being treated may be a human. In some embodiments, the subject being treated may be a non-human mammal. A program comparable to that discussed above may be used in veterinary medicine.

Various pharmaceutical compositions and techniques for their preparation and use will be known to those of skill in the art in light of the present disclosure. For a detailed listing of suitable pharmacological compositions and associated administrative techniques one may refer to the detailed teachings herein, which may be further supplemented by texts such as Remington, *The Science and Practice of Pharmacy*, 20th ed., (Lippincott, Williams & Wilkins 2003). Except insofar as any conventional media or agent is incompatible with the active compound, such use in the compositions is contemplated.

As used herein the language "pharmaceutically acceptable carrier" is intended to include any and all solvents, dispersion media, coatings, isotonic and absorption delaying agents, and the like, compatible with pharmaceutical administration. A "pharmaceutically acceptable salt" is intended to mean a salt of a free acid or base of a compound represented herein that is non-toxic, biologically tolerable, or otherwise biologically suitable for administration to the subject. See, generally, Berge, et al., *J. Pharm. Sci.*, 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

As used herein, the term "therapeutically effective amount" or "effective amount" refers to an amount of a therapeutic agent that when administered alone or in combination with an additional therapeutic agent to a cell, tissue, or subject is effective to prevent, delay the onset of, or reduce the progression of colorectal tumorigenesis. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. In particular, an effective amount is an amount that inhibits or reduces colorectal tumorigenesis.

Treatment of Colorectal Cancer

In another aspect, the present invention herein provides methods for treating or ameliorating a colorectal cancer in a subject, comprising adjusting the composition of gut microbiota in the subject having the colorectal cancer. In some embodiments, methods disclosed herein consist essentially of adjusting the composition of gut microbiota in a subject having colorectal cancer. In some embodiments, methods disclosed herein consist of adjusting the composition of gut microbiota in a subject having colorectal cancer. In some embodiments, methods disclosed herein are not combined with other pharmaceutical(s), e.g., antibiotics, anti-inflammatory drug(s) or chemotherapeutics, e.g., 5-Fluorouracil, Capecitabine, oxaliplatin, Irinotecan, etc.

In some embodiments, the subject has been diagnosed with colitis-associated colorectal cancer. For example, the subject may have a history of IBD before the diagnosis of colorectal cancer. However, other types of colorectal cancer are also contemplated including, but not limited to, HNPCC, colorectal cancer associated with Gardner syndrome, colorectal cancer associated with FAP, colorectal adenocarcinoma, gastrointestinal carcinoid tumors, gastrointestinal stromal tumors, primary colorectal lymphoma, leiomyosarcoma, melanoma, squamous cell carcinoma, etc.

Subjects at various stages of colorectal cancer may be treated with the presently disclosed methods. For example, a subject may be treated with the presently disclosed methods at the precancer or tumor budding stage, at the dysplasia stage, before or after the tumor invades submucosa, before or after the tumor invades muscularis propria, before or after the tumor invades subserosa or beyond, before or after the tumor invades adjacent organs, before or after the tumor perforates the visceral peritoneum, before or after metastasis, before or after surgery, radiation therapy or chemotherapy, before or after remission, etc.

In some embodiments, adjusting the composition of gut microbiota in the subject includes administering the subject a composition comprising bacteria, for example, a composition comprising *Bacteroides* bacteria. In some embodiments, the *Bacteroides* bacteria comprise *B. fragilis, B. thetaiotaomicron, B. vulgatus*, or a mixture thereof. In some embodiments, the composition may comprise *B. fragilis* and *B. thetaiotaomicron*. In some embodiments, the composition may comprise *B. fragilis* and *B. vulgatus*. In some embodiments, the composition may comprise *B. thetaiotaomicron* and *B. vulgatus*. In some embodiments, the *Bacteroides* bacteria can be *B. fragilis*. The composition comprising bacteria, for example a composition comprising *Bacteroides* bacteria, can be administered to the subject via various routes. For example, the composition can be administered to the subject via oral administration, rectal administration, transdermal administration, intranasal administration or inhalation. In some embodiments, the composition is administered to the subject orally. The composition comprising bacteria, such as *Bacteroides* bacteria, can also be in various forms. For example, the composition can be a probiotic composition, a neutraceutical, a pharmaceutical composition, or a mixture thereof.

A variety of parameters may be used to characterize the therapeutic effect of the methods disclosed herein. For example, the therapeutic effect may be characterized as the slowing or stopping of tumor growth in the treated subject, the reduction in tumor number or mass in the treated subject, loss of invasiveness of tumors in the treated subject, or a combination thereof. In some embodiments, the tumors may be tumors of distal colon, proximal colon, or both. To characterize the therapeutic effect, a reference value may be established based on a control subject that is not treated with the methods disclosed herein or the treated subject prior to treatment. In some embodiments, the treated subject may show a decrease of about 5%, about 10%, about 15%, about 20%, about 25%, about 30%, about 35%, about 40%, about 45%, about 50%, about 60%, about 70%, about 80%, about 90%, about 95%, about 99% or about 100%, or a range between any two of these values in the tumor growth in comparison to the reference value. In some embodiments, the treated subject may show a decrease of about 5%, about 10%, about 15%, about 20%, about 25%, about 30%, about 35%, about 40%, about 45%, about 50%, about 60%, about 70%, about 80%, about 90%, about 95%, about 99% or about 100%, or a range between any two of these values in the tumor number or tumor mass in comparison to the reference value. In some embodiments, the treated subject may show a decrease of about 5%, about 10%, about 15%, about 20%, about 25%, about 30%, about 35%, about 40%, about 45%, about 50%, about 60%, about 70%, about 80%, about 90%, about 95%, about 99% or about 100%, or a range between any two of these values in the tumor invasiveness in comparison to the reference value.

Other than colorectal cancer, other types of cancer or cancer-like diseases such as small intestinal adenocarcinoma, Squamous cell carcinoma of the anus, cholangiocarcinoma, hepatobiliary cancers, and hematologic malignancies such as leukemia, hematopoietic cancer, lymphoma, myeloid leukemia may also be treated by the methods disclosed herein.

In some embodiments, the methods comprises identifying the subject in need of treatment based on the type of colorectal cancer, development history of the colorectal cancer, presence of dysbiosis, or a combination thereof. In some embodiments, the composition comprises Vitamin D, ZPS, or a combination thereof. In some embodiments, the composition is administered orally, via fecal transplantation, etc. In some embodiments, the composition may be administered one time, intermittently, chronically, or continuously.

In the methods disclosed herein, the amount of bacteria, for example *Bacteroides* bacteria (e.g., *B. fragilis*), administered to the subject in need of treatment can be determined according to various parameters such as the age, body weight, response of the subject, condition of the subject to be treated; the type and severity of the colorectal cancer; the form of the composition in which the bacteria is included; the route of administration; and the required regimen. The severity of the colorectal cancer may, for example, be evaluated, in part, by standard prognostic evaluation methods. For example, the amount of bacteria can be titrated to determine the effective amount for administering to the subject in need of treatment. One of ordinary skill in the art would appreciate that the attending physician would know how to and when to terminate, interrupt or adjust administration of bacteria due to toxicity or organ dysfunctions. Conversely, the attending physician would also know to adjust treatment to higher levels if the clinical response were not adequate (precluding toxicity).

Relieving Gastrointestinal (GI) Distress

In a further aspect, the present invention herein provides methods for relieving gastrointestinal (GI) distress of a subject having a colorectal condition, comprising: determining the colorectal condition of the subject; and relieving GI distress in the subject by adjusting the composition of gut microbiota in the subject. In some embodiments, methods disclosed herein consist essentially of adjusting the composition of gut microbiota in a subject having a colorectal condition. In some embodiments, methods disclosed herein consist of adjusting the composition of gut microbiota in a subject having a colorectal condition. In some embodiments, methods disclosed herein are not combined with other pharmaceutical(s), e.g., antibiotics, anti-inflammatory drug(s) or chemotherapeutics, e.g., 5-Fluorouracil, Capecitabine, oxaliplatin, Irinotecan, etc.

In some embodiments, the GI distress comprises abdominal cramps, chronic diarrhea, constipation, intestinal permeability, or a combination thereof. In some embodiments, the methods can include reducing intestinal permeability in the subject.

In some embodiments, adjusting the composition of gut microbiota in the subject includes administering the subject a composition comprising bacteria, for example, a composition comprising *Bacteroides* bacteria. In some embodiments, the *Bacteroides* bacteria comprise *B. fragilis, B. thetaiotaomicron, B. vulgatus*, or a mixture thereof. In some embodiments, the composition may comprise *B. fragilis* and *B. thetaiotaomicron*. In some embodiments, the composition may comprise *B. fragilis* and *B. vulgatus*. In some embodiments, the composition may comprise *B. thetaiotaomicron* and *B. vulgatus*. In some embodiments, the *Bacteroides* bacteria can be *B. fragilis*. The composition comprising bacteria, for example a composition comprising *Bacteroides* bacteria, can be administered to the subject via various routes. For example, the composition can be administered to the subject via oral administration, rectal administration, transdermal administration, intranasal administration or inhalation. In some embodiments, the composition is administered to the subject orally. The composition comprising bacteria, such as *Bacteroides* bacteria, can also be in various forms. For example, the composition can be a probiotic composition, a neutraceutical, a pharmaceutical composition, or a mixture thereof.

In some embodiments, the methods comprises identifying the subject in need of treatment based on abdominal cramps, chronic diarrhea, constipation, intestinal permeability, or a combination thereof. In some embodiments, the composition comprises Vitamin D, ZPS, or a combination thereof. In some embodiments, the composition is administered orally, via fecal transplantation, etc. In some embodiments, the composition may be administered one time, intermittently, chronically, or continuously.

In the methods disclosed herein, the amount of bacteria, for example Bacteroides bacteria (e.g., B. fragilis), administered to the subject in need of treatment can be determined according to various parameters such as the age, body weight, response of the subject, condition of the subject to be treated; the type and severity of the colorectal cancer; the form of the composition in which the bacteria is included; the route of administration; and the required regimen. The severity of the colorectal cancer may, for example, be evaluated, in part, by standard prognostic evaluation methods. For example, the amount of bacteria can be titrated to determine the effective amount for administering to the subject in need of treatment. One of ordinary skill in the art would appreciate that the attending physician would know how to and when to terminate, interrupt or adjust administration of bacteria due to toxicity or organ dysfunctions. Conversely, the attending physician would also know to adjust treatment to higher levels if the clinical response were not adequate (precluding toxicity).

EXAMPLES

Some aspects of the embodiments discussed above are disclosed in further detail in the following examples, which are not in any way intended to limit the scope of the present disclosure.

Experimental Material and Methods

The following experimental methods were used for Examples 1-5 described below.

Animals and AOM-Induced Colon Cancer

Azoxymethane (AOM)/dextran sulfate sodium (DSS)-induced colon cancer mouse model was used to study whether PSA can protect mice from colitis-induced colorectal tumorigenesis. A single AOM injection with three cycles of DSS administration was used to induce colon cancer that mimics colitis-driven tumor development. Mice were treated orally with B. fragilis or B. fragilis ΔPSA three times a week starting a week prior to AOM injection until the end of experiment. After initial AOM intraperitoneal injection, 2.5% DSS was given in the drinking water for 6 days followed by regular drinking water. Mice were subjected to a second DSS cycle with 2.5% DSS water at day 25 for 6 days and a third cycle with 1.5% DSS water at day 55 for 4-6 days. Mice were sacrificed on days 81 post AOM injection.

B. fragilis Colonization Assay

Fecal samples are sterilely collected from mice at 1, 2 and 3 weeks after the start of treatment with B. fragilis or vehicle. DNA is isolated fecal samples using the QIAamp DNA Stool Mini Kit (Qiagen). 50 ng DNA is used for qPCR with B. fragilis-specific primers 5' TGATTCCGCATG-GTTTCATT 3' (SEQ ID NO: 1) and 5' CGACCCATA-GAGCCTTCATC 3' (SEQ ID NO: 2), and universal 16S primers 5' ACTCCTACGGGAGGCAGCAGT 3' (SEQ ID NO: 3) and 5' ATTACCGCGGCTGCTGGC 3' (SEQ ID NO: 4) according to Odamaki et al., Appl. Environ. Microbiol. 74: 6814-17 (2008).

Example 1

Figure 1:
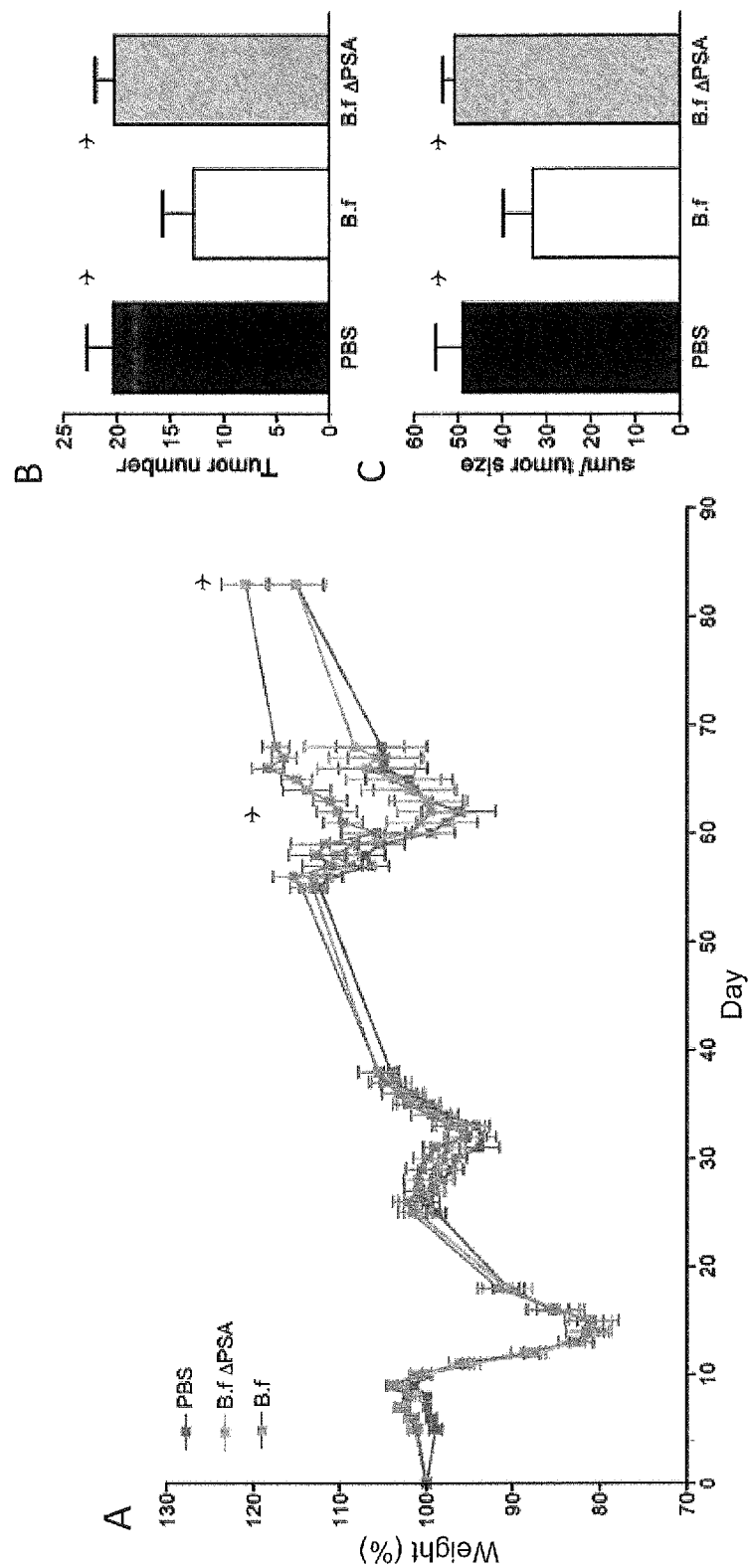
FIG. 1 shows colonization of azoxymethane (AOM)/dextran sulfate sodium (DSS) treated mice with *B. fragilis* protects from the development of colon cancer, compared to mice colonized with *B. fragilis* ΔPSA (a mutant in *B. fragilis* only of the genes required to produce PSA) or control group. (A) *B. fragilis* or *B. fragilis* ΔPSA was orally administered to mice and monitored for weight loss during DSS water treatment. Mice with PBS or *B. fragilis* ΔPSA colonization showed significantly increased weight loss during the third DSS treatment period compared to mice with *B. fragilis* colonization. (B, C) The number of tumors and the sum of tumor size in *B. fragilis* colonized mice were also significantly decreased compared to control and *B. fragilis* ΔPSA colonized groups.

Colonization with B. fragilis Protects Mice from the Development of Colon Cancer To examine the role of B. fragilis colonization and PSA during the development of colorectal cancer, 8 week old mice were given B. fragilis or B. fragilis ΔPSA orally and monitored for weight loss during DSS water treatment. Mice treated with PBS or B. fragilis ΔPSA showed significantly increased weight loss during the third cycle of DSS treatment compared to mice with B. fragilis (FIG. 1A). It indicates the protective effect of B. fragilis colonization and PSA during the development of colitis-induced colon cancer. The number of tumors and the sum of tumor size in B. fragilis colonized mice were also significantly decreased compared to control and B. fragilis ΔPSA groups (FIGS. 1B & 1C). These results indicate that colonization of B. fragilis protects mice against colitis-induced colorectal tumorigenesis in a PSA dependent manner. The finding is especially remarkable because B. fragilis did not protect against DSS-induced colitis in a mouse model (data not shown).

Example 2

Figure 2:
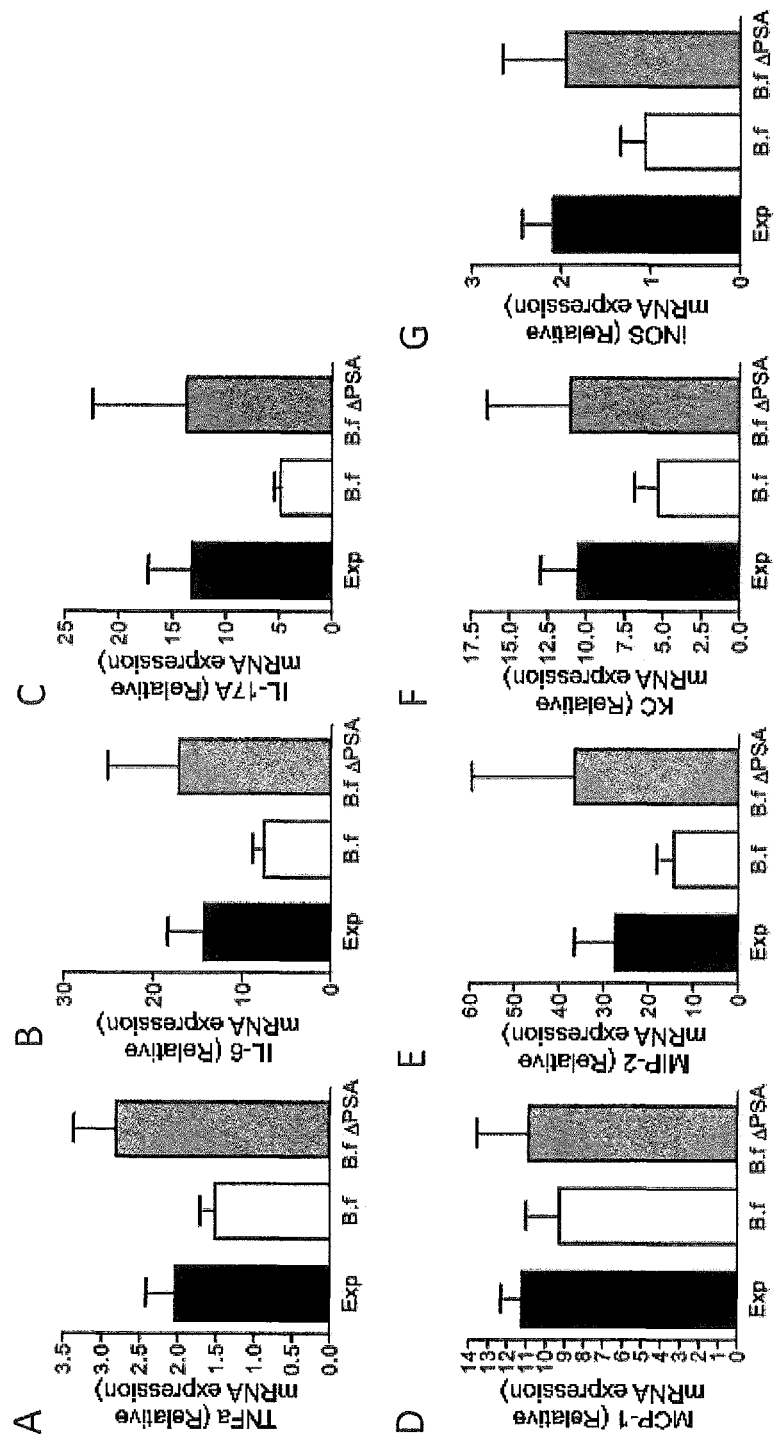
FIG. 2 shows the effect of *B. fragilis* colonization on the expression of pro-inflammatory cytokines and signature genes during colon cancer development. (A) Comparison of TNF-α level among control, mice colonized with *B. fragilis* and mice colonized with *B. fragilis* ΔPSA. (B) Comparison of IL-6 level among control, mice colonized with *B. fragilis* and mice colonized with *B. fragilis* ΔPSA. (C) Comparison of IL-17A level among control, mice colonized with *B. fragilis* and mice colonized with *B. fragilis* ΔPSA. (D) Comparison of MCP-1 level among control, mice colonized with *B. fragilis* and mice colonized with *B. fragilis* ΔPSA. (E) Comparison of MIP-2 level among control, mice colonized with *B. fragilis* and mice colonized with *B. fragilis*

B. fragilis Colonization Inhibits the Expression of Pro-Inflammatory Cytokines and Signature Genes During Colon Cancer Development Monocyte chemoattractant protein 1 (MCP-1), macrophage inflammatory protein 2 (MIP-2) and KC (also called chemokine ligand 1; CXCL1) are key chemokines that are often observed during inflammation. Expression of inducible nitric oxide synthase (iNOS) has also been observed during colon carcinogenesis. The expression level of proinflammatory cytokines, chemokines and iNOS from colon homogenates of B. fragilis or B. fragilis ΔPSA colonized mice were examined. Colonic tissues from B. fragilis colonized mice expressed significantly lower level of TNFα, IL-6, IL-17A, MCP-1, MIP-2, KC and iNOS compared to untreated controls and B. fragilis ΔPSA colonized mice (FIG. 2). It indicates that B. fragilis colonization and PSA regulate the expression level of pro-inflammatory cytokines, chemokines and iNOS during the development of colon cancer.

Example 3

TLR2 Signalling is Required for the Protection from Development of Colon Cancer by B. fragilis Colonization PSA of B. fragilis has been shown to utilize TLR2 signalling to regulate inflammatory responses (Wang et al., J. Exp. Med. 203: 2853-63 (2006)). TLR2 signalling was tested to see whether it is required for the protection of the development of colon cancer in mice colonized by B. fragilis. WT mice colonization with B. fragilis showed significantly decreased weight loss compared to mice treated PBS, whereas TLR2$^{-/-}$ mice showed similar degree of weight loss regardless of B. fragilis colonization (FIG. 3A). The number of tumors in distal colon was significantly decreased in WT mice colonized with B. fragilis compared to WT mice treated with PBS, whereas TLR2$^{-/-}$ mice developed similar number of tumors in distal colon regardless of B. fragilis colonization (FIG. 3B). More tumors were found in proximal colon of TLR2$^{-/-}$ mice with or without B. fragilis colonization in comparison to WT (FIG. 3C). These results indicate the protection from colitis-induced colon cancer by B. fragilis colonization is through the TLR2 signalling pathway.

Example 4

Prevention of Colitis-Induced Colorectal Tumorigenensis in Mice by PSA

To examine the protective effect of PSA during the development of colitis-induced colorectal cancer, 8 week old mice are given PSA or PBS orally and monitored for weight loss during DSS water treatment. Mice treated with PBS show significantly increased weight loss during the third cycle of DSS treatment compared to mice treated with PSA. The number of tumors and the sum of tumor size in PSA treated mice are also significantly decreased compared to control mice.

Example 5

Treatment of Colitis-Associated Colorectal Cancer in Mice by B. fragilis Colonization To examine the effect of B. fragilis colonization on colitis-associated colorectal cancer, AOM/DSS-induced colon cancer or genetically engineered IBD mouse models are used (see, e.g., Tong et al., *Chin. J. Cancer* 30: 450-62 (2011), the content of which is herein expressly incorporated by reference in its entirety). Mice having colorectal cancer are colonized with B. fragilis by fecal transplantation or oral administration. B. fragilis colonization of mouse is monitored during treatment period. The status of colorectal cancer, including the size of tumor, number of tumors, tumor growth, tumor remission, and progression to metastasis, etc., is recorded and compared between the treatment and control groups.

Example 6

Prevention of Colorectal Tumorigenensis in Chronic Ulcerative Colitis Patients by Colonization of B. fragilis Patients diagnosed with chronic ulcerative colitis are treated with B. fragilis to determine the preventative effect of adjusting the composition of gut microbiota on colorectal tumorigenesis. B. fragilis is administered orally to the patients. A control group of patients is treated with a placebo. The composition of the patients' gut microbiota is monitored throughout the treatment period. Administration of B. fragilis is suspended after successful colonization of patient's colon by B. fragilis. The status of colorectal tumorigenesis, including the onset of tumor, type of tumor, size of tumor, number of tumors, and response or lack thereof to treatment regimens is recorded and compared between the treatment and control groups.

Example 7

Prevention of Colorectal Tumorigenesis in Chronic Ulcerative Colitis Patients by PSA Patients diagnosed with chronic ulcerative colitis are treated with a pharmaceutical composition of PSA to determine the preventative effect of PSA on colorectal tumorigenesis. Oral administration is used to introduce the pharmaceutical composition of PSA into the patients. A control group of patients is treated with placebo. The status of colorectal tumorigenesis, including the onset of tumor, type of tumor, size of tumor, number of tumors, and response or lack thereof to treatment regimens is recorded and compared between the treatment and control groups.

The foregoing description and examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof. Although the present application has been described in detail above, it will be understood by one of ordinary skill in the art that various modifications can be made without departing from the spirit of the invention.

All references cited herein including, but not limited to, published and unpublished patent applications, patents, text books, literature references, and the like, to the extent that they are not already, are hereby incorporated by reference in their entirety. To the extent that one or more of the incorporated literature and similar materials differ from or contradict the disclosure contained in the specification, including but not limited to defined terms, term usage, described techniques, or the like, the specification is intended to supersede and/or take precedence over any such contradictory material.

What is claimed is:

1. A method of preventing or reducing the development of colorectal cancer in a subject identified as at risk of colorectal tumorigenesis, comprising:
   administering to the subject a composition comprising a polysaccharide A (PSA) whose structure includes the repeating unit [→3) α-d-AATGalp(1→4)-[β-d-Galf (1→3)] α-d-GalpNAc(1→3)[4,6-pyruvate]-βd-Galp (1→} wherein AATGal is acetamido-amino-2,4,6-trideoxygalactose, and the galactopyranosyl residue is modified by a pyruvate spanning O-4 and O-6, in an amount effective to prevent or reduce the development of colorectal cancer, thereby the tumor-free period of the subject is increased by at least 5% in comparison to a subject to which the composition has not been administered, or the tumor growth in the subject is reduced by at least 5% in comparison to a subject to which the composition has not been administered, or both; and
   wherein the method does not comprise administering to the subject an antibiotic.

2. The method of claim 1, wherein the composition is a probiotic composition, a nutraceutical composition, a pharmaceutical composition, or a mixture thereof.

3. The method of claim 1, wherein the composition is administered via oral administration.

4. The method of claim 1, wherein the composition is administered intermittently, periodically, continuously, or chronically.

5. The method of claim 1, wherein the composition is administered following assessing the risk of colorectal tumorigenesis of the subject.

6. The method of claim 5, wherein assessing the risk of colorectal tumorigenesis of the subject is performed by looking for a family history of colorectal cancer of the subject, identifying a genetic mutation associated with colorectal cancer in the subject, testing for dysbiosis in the subject, or a combination thereof.

7. The method of claim 6, wherein the dysbiosis comprises an over-representation of *Proteus mirabilis* and/or *Klebsiella pneumonia*.

8. The method of claim 1, wherein the tumor-free time of the subject is increased by at least 20% in comparison to a reference tumor-free time in one or more subjects to which the composition is not administered.

9. The method of claim 1, wherein the tumor growth in the subject is decreased by at least 20% in comparison to a reference tumor growth in one or more subjects to which the composition has not been administered.

10. The method of claim 1, wherein the total tumor number in the subject is decreased by at least 20% in comparison to a reference total tumor number in one or more subjects to which the composition has not been administered.

11. The method of claim 1, wherein the PSA is isolated PSA.

12. The method of claim 11, wherein the PSA is isolated from *Bacteroides fragilis*.

13. The method of claim 1, wherein the composition comprises *Bacteroides fragilis* bacteria.

14. The method of claim 1, wherein the composition further comprised Vitamin D.

15. The method of claim 1, wherein the composition is administered in combination with one or more therapeutic agents.

16. The method of claim 15, wherein the composition and one or more therapeutic agents are for administration simultaneously or consecutively in any order.

17. The method of claim 15, where the composition and one or more therapeutic agents are for administration chronically or intermittently.

18. The method of claim 1, wherein the tumor growth in the subject comprises increase in total tumor number, increase in total tumor size, increase in total tumor mass, increase in invasiveness of the tumor.

19. The method of claim 18, wherein the increase in total tumor size in the subject is decreased by at least 20% in comparison to one or more subjects to which the composition has not been administered.

20. The method of claim 18, wherein the increase in total tumor mass in the subject is decreased by at least 20% in comparison to one or more subjects to which the composition has not been administered.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
tgattccgca tggtttcatt                                               20

<210> SEQ ID NO 2
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 2
cgacccatag agccttcatc                                          20

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
actcctacgg gaggcagcag t                                        21

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
attaccgcgg ctgctggc                                            18
```